US 6,221,049 B1

(12) United States Patent
Selmon et al.

(10) Patent No.: US 6,221,049 B1
(45) Date of Patent: *Apr. 24, 2001

(54) METHODS AND APPARATUS FOR CROSSING VASCULAR OCCLUSIONS

(75) Inventors: Matthew R. Selmon, Atherton; Charles F. Milo, San Mateo; Fred Co, Santa Clara; Mark Campello, Millbrae; Ronald French; Amiel Aguilar, both of Palo Alto, all of CA (US)

(73) Assignee: Lumend, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/427,966

(22) Filed: Oct. 27, 1999

Related U.S. Application Data

(60) Division of application No. 09/163,854, filed on Sep. 30, 1998, which is a continuation-in-part of application No. 09/006,563, filed on Jan. 13, 1998.

(51) Int. Cl.$^7$ .......................... A61M 5/178; A61M 5/32; A61B 5/00

(52) U.S. Cl. ...................... 604/164.13; 604/272; 600/585

(58) Field of Search ......................... 604/164.01, 164.05, 604/164.11, 164.13, 165.01–165.04, 166.01, 171, 172, 198, 272, 507, 508, 510, 528; 606/108, 159; 600/585

(56) References Cited

U.S. PATENT DOCUMENTS

| | | |
|---|---|---|
| 1,747,407 | 2/1930 | Wappler . |
| 4,405,314 | 9/1983 | Cope ....................................... 604/51 |
| 4,552,554 | 11/1985 | Gould et al. ............................ 604/51 |

(List continued on next page.)

FOREIGN PATENT DOCUMENTS

| | | | |
|---|---|---|---|
| 2945237 A1 U | 5/1981 | (DE) | A61B/17/22 |
| 4429117 A1 | 2/1996 | (DE) | A61M/29/00 |
| 0 377 269 A1 | 7/1990 | (EP) . | |

(List continued on next page.)

OTHER PUBLICATIONS

Melchior, J. et al., "Percutaneous Transluminal Coronary Angioplasty for Chronic Total Coronary Arterial Occlusion", *American Journal of Cardiology*, vol. 59, (1987), pp. 535–538.

Meier, B., "Total Coronary Occlusion: A Different Animal?", *Journal of the American College of Cardiology*, vol. 17, No. 6, May 1991, pp. 50B–57B.

Puma, J. et al., "Percutaneous Revascularization of Chronic Coronary Occlusions: An Overview", *JACC*, vol. 26, No. 1, Jul. 1995, pp. 1–11.

(List continued on next page.)

Primary Examiner—Sharon Kennedy
(74) Attorney, Agent, or Firm—Wilson, Sonsini, Goodrich & Rosati

(57) ABSTRACT

Methods and apparatus for crossing totally to substantially occluded blood vessels by passing a redirectable wire such as a guidewire from a relatively proximal point past the occlusion within a subintimal space formed between the intimal layer and the adventitial layer of a blood vessel wall. The wire may be advanced to a point distal to the occlusion, and thereafter deflected back into the blood vessel lumen, typically using a deflecting catheter which is advanced over the guidewire after it has been positioned within the subintimal space. The deflecting catheter may include a flapper valve assembly or preformed actuator wire for redirecting the guidewire. After the guidewire is returned to the blood vessel lumen, the deflecting catheter may be withdrawn, and the guidewire may be available for introduction of other interventional and diagnostic catheters for performing procedures such as stenting.

8 Claims, 20 Drawing Sheets

U.S. PATENT DOCUMENTS

| | | | |
|---|---|---|---|
| 4,648,402 | 3/1987 | Santos | 128/345 |
| 4,774,949 | 10/1988 | Fogarty | 128/348.1 |
| 4,947,864 | 8/1990 | Shockey et al. | 128/772 |
| 5,001,556 | 3/1991 | Nakamura et al. | 358/98 |
| 5,019,040 | 5/1991 | Itaoka et al. | 604/95 |
| 5,061,245 | 10/1991 | Waldvogel | 604/170 |
| 5,095,911 | 3/1992 | Pomeranz | 128/662.06 |
| 5,099,850 | 3/1992 | Matsui et al. | 128/662.06 |
| 5,109,830 | 5/1992 | Cho | 128/4 |
| 5,114,414 | 5/1992 | Buchbinder | 604/95 |
| 5,127,917 | 7/1992 | Niederhauser et al. | 606/191 |
| 5,183,470 | 2/1993 | Wettermann | 604/281 |
| 5,190,528 | 3/1993 | Fonger et al. | 604/171 |
| 5,279,565 | 1/1994 | Klein et al. | 604/105 |
| 5,287,861 | 2/1994 | Wilk | 128/898 |
| 5,321,501 | 6/1994 | Swanson et al. | 356/345 |
| 5,350,377 | 9/1994 | Winston et al. | 606/15 |
| 5,389,096 | 2/1995 | Aita et al. | 606/15 |
| 5,409,019 | 4/1995 | Wilk | 128/898 |
| 5,409,453 | 4/1995 | Lundquist et al. | 604/22 |
| 5,413,581 | 5/1995 | Goy | 606/194 |
| 5,429,144 | 7/1995 | Wilk | 128/898 |
| 5,443,497 | 8/1995 | Venbrux | 623/1 |
| 5,452,733 | 9/1995 | Sterman et al. | 128/898 |
| 5,456,694 | 10/1995 | Marin et al. | 606/198 |
| 5,456,714 | 10/1995 | Owen | 623/1 |
| 5,464,395 | 11/1995 | Faxon et al. | 604/96 |
| 5,486,170 | 1/1996 | Winston et al. | 606/16 |
| 5,573,531 | 11/1996 | Gregory | 606/14 |
| 5,607,435 | 3/1997 | Sachdeva et al. | 606/139 |
| 5,628,761 | 5/1997 | Rizik | 606/170 |
| 5,695,457 | 12/1997 | St. Goar et al. | 604/4 |
| 5,707,389 | 1/1998 | Louw et al. | 606/200 |
| 5,741,270 | 4/1998 | Hansen et al. | 606/106 |
| 5,910,133 | 7/1999 | Gould | 604/164 |
| 5,935,108 | 8/1999 | Katoh et al. | 604/164 |
| 5,938,671 | 8/1999 | Katoh et al. | 606/159 |
| 6,015,423 | 1/2000 | Andrese | 606/198 |

FOREIGN PATENT DOCUMENTS

| | | | |
|---|---|---|---|
| 1585065 | 9/1970 | (FR) | . |
| WO 83/03188 | 9/1983 | (WO) | A61B/1/06 |
| WO 91/19528 | 12/1991 | (WO) | A61M/29/00 |
| WO 92/08510 | 5/1992 | (WO) | A61M/25/00 |
| WO 93/18818 | 9/1993 | (WO) | A61M/37/00 |
| WO95/02430 | 1/1995 | (WO) | . |
| WO 95/19143 | 7/1995 | (WO) | A61B/17/22 |
| WO 96/01590 | 1/1996 | (WO) | A61B/17/22 |
| WO96/04035 | 2/1996 | (WO) | A61M/25/14 |
| WO 97/13463 | 4/1997 | (WO) | A61B/17/00 |
| WO 97/13471 | 4/1997 | (WO) | A61B/19/00 |
| WO 97/26936 | 7/1997 | (WO) | A61M/25/01 |
| WO 97/27893 | 8/1997 | (WO) | A61M/19/00 |
| WO 97/27897 | 8/1997 | (WO) | A61M/29/00 |
| WO 97/27898 | 8/1997 | (WO) | A61M/29/00 |
| WO 97/37581 | 10/1997 | (WO) | . |
| WO97/44083 | 11/1997 | (WO) | . |
| WO 98/08456 | 3/1998 | (WO) | . |
| WO 98/16161 | 4/1998 | (WO) | . |

OTHER PUBLICATIONS

Werner, G. et al., "Vessel Reconstruction in Total Coronary Occlusions With a Long Subintimal Wire Pathway: Use of Multiple Stents Under Guidance of Intravascular Ultrasound", *Catheterization and Cardiovascular Diagnosis*, vol. 40, pp. 46–51 (1997).

Sirnes, P. et al., "Stenting in Chronic Coronary Occlusion (SICCO): A Randomized, Controlled Trial of Adding Stent Implantation After Successful Angioplasty", *JACC*, vol. 28, No. 6, Nov. 1996, pp. 1444–1451.

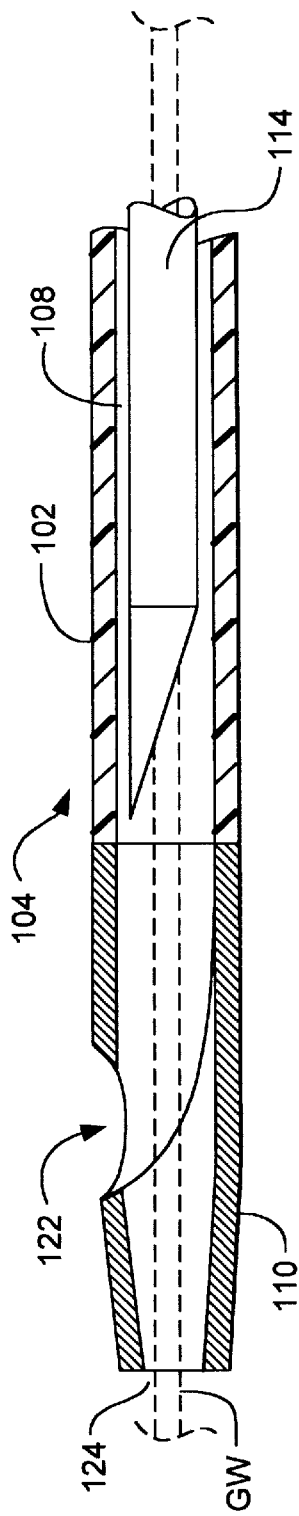
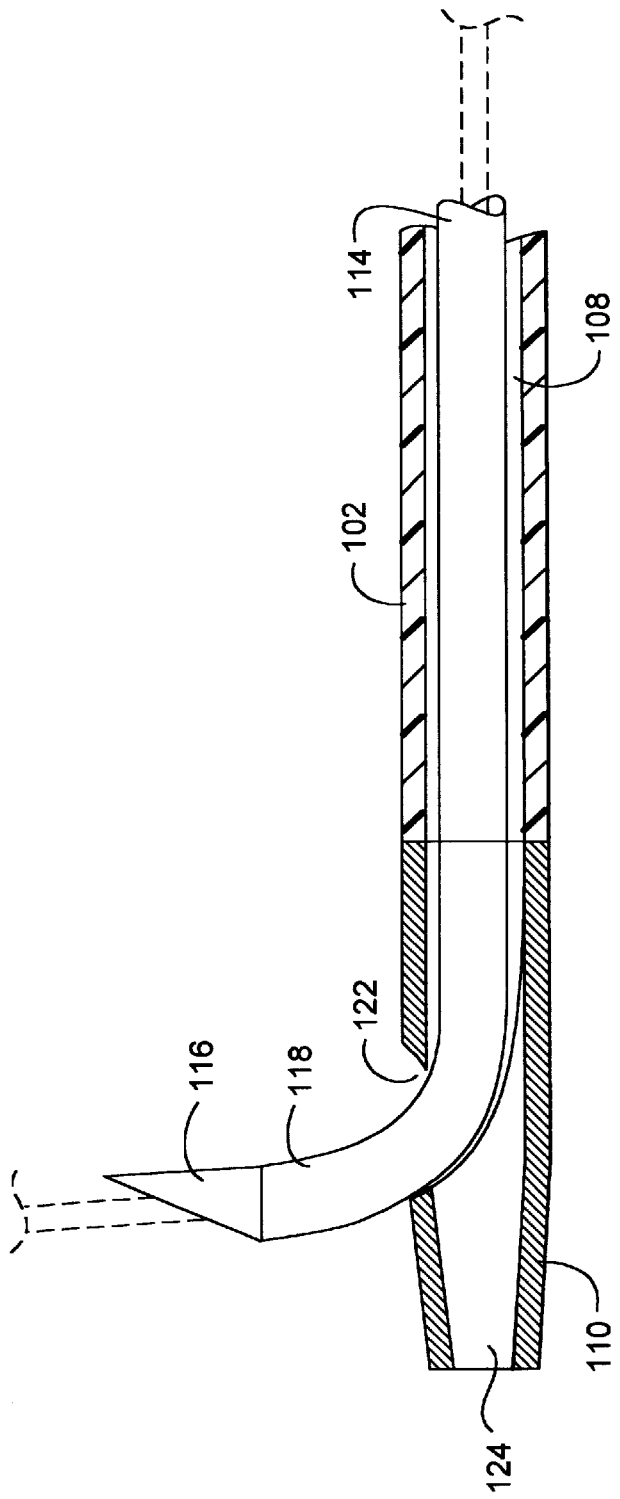

METHODS AND APPARATUS FOR CROSSING VASCULAR OCCLUSIONS

This application is a Division of U.S. Application No. 09/163,854 filed Sep. 30, 1998, now allowed, which is a Continuation-In-Part of U.S. Application 09/006,563 filed Jan. 13, 1998, now allowed.

FIELD OF THE INVENTION

The present invention relates generally to medical devices, kits, and methods used in the treatment of vascular occlusions. More particularly, the invention relates to systems and procedures for crossing chronic occlusions in blood vessels with guidewires that may facilitate performance of subsequent treatment and therapies including angioplasty, atherectomy and stenting procedures.

BACKGROUND OF THE INVENTION

Cardiovascular disease is a leading cause of mortality worldwide that can take on many different forms. A particularly troublesome form of cardiovascular disease results when a blood vessel becomes totally occluded with atheroma or plaque, referred to as a chronic total occlusion. Until recently, chronic total occlusions have usually been treated by performing a bypass procedure where an autologous or synthetic blood vessel is anastomotically attached to locations on the blood vessel upstream and downstream of the occlusion. While highly effective, such bypass procedures are quite traumatic to the patient. Recently, catheter-based intravascular procedures have been utilized to treat chronic total occlusions with increasing success. Catheter-based intravascular procedures include angioplasty, atherectomy, stenting, and the like, and are often preferred because they are much less traumatic to the patient. Before such catheter-based treatments can be performed, however, it is usually necessary to cross the occlusion with a guidewire to provide access for the interventional catheter. In some instances, crossing the occlusion with a guidewire can be accomplished simply by pushing the guidewire through the occlusion. The guidewire remains in the blood vessel lumen and provides the desired access path. In many cases, however, the guidewire inadvertently penetrates into the subintimal space between the intimal layer and the adventitial layer of the blood vessel as it attempts to cross the occlusion. Once in the subintimal space, it is very difficult and impossible in many instances to direct the guidewire back into the blood vessel lumen. In such cases, it will usually be impossible to perform the catheter-based intervention and other procedures may have to be employed that are relatively more traumatic. Catheters and methods for forming lateral penetrations through tissue to and from blood vessels past total occlusions are described in U.S. Pat. Nos. 5,443,497; 5,429,144; 5,409,019; 5,287,861; WO 97/13463; and WO 97/13471. Catheters having side guidewire entry ports spaced proximally from their distal tips are also described in U.S. Pat. Nos. 5,464,395; 5,413,581; 5,190,528; 5,183,470; 4,947,864; and 4,405,314. These and a variety of other specific interventional and pharmaceutical treatments have been devised over the years with varying levels of success for different applications.

SUMMARY OF THE INVENTION

The present invention provides methods and apparatus for crossing substantial or total occlusions in blood vessels. It is an object of the invention to traverse vascular occlusions or other blockages formed within blood vessels in order to provide pathways for the placement of guidewires or other interventional devices as part of an overall effort to restore or provide adequate circulation. It is advantageous to cross a substantially occluded blood vessel by finding and/or creating a path with the least or relatively low resistance through or around at least a portion of the occlusion which may include travel along or between the layers of a blood vessel wall in regions such as the subintimal space. The invention further provides methods, kits, and apparatus which facilitate crossing a chronic total occlusion in a blood vessel with a guidewire. In particular, catheters, guides, or other apparatus provided herein may be used with conventional or specialized guidewires to direct or redirect the guidewires from a subintimal space, or other areas between the different layers of a blood vessel wall, back into the blood vessel lumen. The disclosed apparatus include devices formed with relatively simple construction, and may be used in a relatively straight-forward manner.

One aspect of the invention provides apparatus for crossing a vascular occlusion by directing a lead device such as a guidewire around at a least a portion of the obstruction within the blood vessel wall. A deflecting catheter may controllably deflect or direct the guidewire through or around a vascular occlusion formed within the natural lumen of the vessel, and may direct the guidewire within a region in between the various layers of the vessel wall to completely or partially circumvent the blockage. The deflecting catheter may provide any combination of these controllable movements to position the guidewire in a manner that can facilitate interventional treatments such as stenting. Another variation of the invention includes a guidewire deflection system comprising a catheter body formed with at least one lumen extending along its length, a nosecone formed at the distal end of the catheter body having a distal and a lateral opening. The region surrounding the lateral opening may include an adjacent inclined surface. The distal opening and the lateral opening are both in communication with the catheter body lumen. In addition, a cannula may be included having a cannula port in communication with at least one passageway extending through at least a distal portion of the cannula. The distal end of the cannula may be configured to communicate with the inclined surface adjacent to the lateral opening to deflect the cannula away from the longitudinal axis of the catheter body. The distal portion of the cannula may further have a pre-formed shape resilient curve, and may be slidably positioned within the lumen of the catheter body. The distal portion may have a relatively axially aligned configuration with the lumen when the cannula is positioned within the catheter body, and a relatively curved configuration with the lumen when the cannula travels along the inclined surface and through the lateral opening of the catheter body when the cannula is distally advanced through the lumen within the catheter body. The guidewire deflection system may further comprise a guidewire configured to pass through the passageway of the cannula. A variety of imaging components or markers may be also positioned on various portions of the wire, cannula or catheter body. A hub assembly rotationally secured to the proximal end of the catheter body may be selected to controllably rotate the cannula and the catheter body.

In yet another embodiment of the invention, an intravascular catheter is provided having a catheter shaft formed with at least one longitudinal lumen. A nosecone may be positioned at the distal end of the catheter shaft having a first port in communication with the longitudinal lumen formed with a first cross-sectional area, and a second port in communication with the longitudinal lumen formed with a second cross-sectional area, wherein the first cross-sectional area is relatively larger that the second cross-sectional area., A cannula may be slidably positioned within at least a portion of the longitudinal lumen of the catheter shaft, and may be configured for passage through the first port which is relatively larger, but not through the second port of the nosecone which is relatively smaller in size. A guidewire may be also slidably positioned within at least a portion of the cannula passageway, and may be configured for passage through an inclined surface formed adjacent to the second port. The nosecone may further include imaging components or radiopaque markers that provides directional orientation.

Another embodiment of the invention provides a redirectable intravascular guidewire catheter. The catheter may be formed with a catheter shaft and a guidewire deflector formed at the distal end of the catheter shaft. The guidewire deflector may be formed as a nosecone assembly having a distal end port, a lateral port, and a relatively internal or external flapper assembly with a deflectable extension. The deflectable extension of the flapper assembly may have a first position that directs a guidewire tip through the distal end port when the guidewire tip is positioned relatively distal to the deflectable extension. It may further have a second position that directs the guidewire tip through the lateral port when the tip is positioned relatively proximal to the deflectable extension and advanced thereafter in a relatively distal direction. Additionally, a guidewire may be included in the catheter that is slidably positioned within the lumen of the catheter shaft. A portion of the flapper assembly may be also formed of a fluoroscopic material to provide an orientation marker for directional placement of a guidewire.

A redirectable guidewire catheter is further provided in accordance with the concepts of the invention comprising a catheter shaft, an actuator wire, and guidewire. The catheter shaft may be formed with a first lumen and a second lumen each extending along the catheter shaft respectively to a first distal opening and a second distal opening. The actuator wire may be slidably positioned with the first lumen of the catheter shaft, wherein the actuator wire is formed with a preformed distal end to provide an actuated position that is biased towards the second distal opening when advanced relatively distal through the first distal opening. Furthermore, the actuator wire may extend only within or beyond the outer surface of the catheter shaft at a relatively distal or distal most end portion of the catheter shaft. The guidewire may be slidably positioned within the second lumen of the catheter shaft, and may be deflected when advanced relatively distal through the second distal opening when the actuator wire is placed in its actuated position. In another variation of the invention, the redirectable guidewire catheter may have a catheter shaft with a first lumen and a second lumen each extending along the catheter shaft. A nosecone may be formed at the distal portion of the catheter shaft, wherein the nosecone includes a distal orifice and an interior region formed with a tapered surface. The actuator wire may be formed with a distal tip that is slidably positioned with the first lumen of the catheter shaft, wherein the distal tip of the actuator wire is redirected substantially away from the longitudinal axis of the catheter shaft when advanced relatively distal along the tapered surface of the nosecone and through the nosecone orifice. The guidewire may be slidably positioned within the second lumen of the catheter shaft, and may be deflected away from the longitudinal axis of the catheter shaft by contacting the redirected actuator wire when the guidewire is advanced relatively distal through the distal orifice.

Yet another variation of the invention provides an intravascular catheter for selectively deflecting a guidewire that includes a catheter body formed with a distal end and a longitudinal lumen formed along at least a portion of the catheter body. A support tube may be formed with a distal tube end that includes a cut-out portion to accept the distal portion of a cannula. The support tube may be slidably and rotatably positioned within the longitudinal lumen of the catheter body. The cannula may include at least one passageway extending through at least a distal end portion of the cannula, wherein the distal portion of the cannula has a pre-formed shape resilient curve that may communicate with the cut-out portion when the cannula is slidably positioned within the conduit of the support tube. The proximal tube end of the support tube may be connected to a rotating assembly to rotate the support tube relative to the catheter body. Another variation of the intravascular catheter may include a support tube connected to the distal cannula end, wherein the support tube is formed with a distal tube end section, a proximal tube end section, and a backbone connecting the distal and the proximal tube end sections. The support tube or the distal cannula end may be preformed with a predetermined shape to deflect the distal cannula end away from the longitudinal axis of the catheter body when the distal cannula end is extended proximally past the distal end of the catheter body.

Another aspect of the invention provides methods for crossing a substantially occluded blood vessel. The method may include the steps of selecting a guidewire with a deflectable distal tip configured for placement in a blood vessel wall, creating a longitudinal dissection plane within the blood vessel wall by inserting the guidewire into blood vessel wall from within the blood vessel lumen at a proximal location relative to a vascular occlusion, forming a channel along the blood vessel wall by advancing the guidewire in a relatively distal direction along the blood vessel wall, and selectively deflecting the distal tip of the guidewire at a relatively distal location relative to the proximal location back into the blood vessel lumen. An interventional or diagnostic catheter may be advanced over the deflected guidewire from a position relatively proximal to the occlusion, through the channel, and back into the blood vessel lumen.

Other variations of the invention described herein also include methods where total occlusions are crossed by first forming a track or channel from a lumen in a blood vessel into a subintimal space between an intimal layer and an adventitial layer of the blood vessel. The track may be formed so that it extends from a location proximal of the total occlusion to a location which is relatively distal to the total occlusion, or at any positioned located therebetween. A passage may be then formed from the track back into the blood vessel lumen at the relatively distal location. In one variation of the invention, the track may be formed by advancing a wire through the blood vessel lumen into the subintimal space by typically advancing the wire until it encounters the total occlusion. By continuing to advance the wire in a generally distal direction, it may pass into the subintimal space of the blood vessel, and may be further advanced toward a desired distal location. After the wire is located or confirmed at a point relatively distal to the total occlusion or original point of insertion, it may be typically deflected from the track or channel back into the blood vessel lumen.

In some exemplary methods described herein, the wire may be deflected using a deflecting catheter. Typically, the deflecting catheter may be advanced over a proximal end of the wire and advanced into the track within the subintimal space. The wire and the deflecting catheter may be manipulated so that the wire is deflected laterally through the intimal layer back into the blood vessel lumen. Such deflecting catheters may be also useful in axially supporting the wire as it is advanced into and/or through the track, i.e. the catheter can enhance the "pushability" of the wire when it is advanced forward through any resisting material. Specific designs for such deflecting catheters are described in detail below. The wire, which is initially positioned within the track in the subintimal space, may be alternatively withdrawn through the deflecting catheter and exchanged for a second wire or device suitable for penetrating through the intimal layer of the blood vessel wall back into the lumen. It will be appreciated that the wires and/or deflecting and other catheters may be freely exchanged over or through one another in a conventional matter without departing from the scope of the invention.

Various imaging techniques may be used in accordance with the invention to determine where the wire and/or deflecting catheter are positioned with respect to a vascular occlusion so that the wire may be returned to the blood vessel lumen at a desired location or beyond the occlusion. For example, the position determination can be made by fluoroscopically imaging the blood vessel in a conventional manner. Alternatively or additionally to such fluoroscopic imaging, intravascular imaging, e.g. intravascular ultrasonic imaging (IVUS), and a variety of optical imaging modelities, such as optical coherence tomography (OCT), may be employed. For example, an ultrasonic imaging guidewire may be used to initially access the subintimal space and/or may be exchanged for the wire which is used to access the subintimal space. An imaging guidewire present in the subintimal space may readily detect the presence or absence of occluding material within the blood vessel lumen. The transition from detecting occluding material to the lack of the same is a strong indication that the position of the guidewire has advanced beyond the total occlusion. The wire may be deflected thereafter and returned towards the blood vessel lumen. After a passageway is formed from the track or channel back into the blood vessel lumen, and a wire is in place across the total occlusion, the wire may be used as a guidewire for positioning interventional and diagnostic catheters across the obstruction. Interventional catheters are often positioned across the total occlusion for treating the occlusion, and include devices such as angioplasty balloon catheters, rotational atherectomy catheters, directional atherectomy catheters, and stent-placement catheters.

Another aspect of the invention provides methods for crossing a vascular occlusion with a deflecting wire. The wire deflecting step may include deflecting a cannula from the subintimal space of a blood vessel wall back into the blood vessel lumen, and thereafter passing the wire through a path defined by the cannula, typically by a lumen within the cannula. The cannula may be advanced over the wire after the wire is disposed or advanced within the subintimal space, and a cannula-deflecting step may be also included that involves distally advancing a resilient or preformed curved end portion of the cannula from a constraining lumen formed within a surrounding catheter or sheath back into the blood vessel lumen. Alternatively, a wire-deflecting step may comprise advancing a deflecting catheter over the wire which has been advanced into the subintimal space. A cannula may then be advanced through a lateral opening of the deflecting catheter, and penetrate through the intimal layer to define a path for the wire back into the blood vessel lumen. A wide variety of steerable and actively deployed cannulas may also be used in the foregoing applications..

The present invention further provides kits for crossing vascular occlusions comprising a wire-deflecting catheter having a lumen or mechanism capable of laterally deflecting a wire. The kit may further comprise instructions setting forth any of the methods described above. Other methods and apparatus formed in accordance with the invention, as specifically described herein, may be also combined to provide numerous kits for many applications as in the treatment of coronary artery and peripheral vascular occlusions. Optionally, the kits provided herein may further comprise a wire for penetrating into the subintimal space and/or back into the blood vessel lumen. The kit may still further comprise a package for containing a wire deflecting catheter, instructions for its use as described in the various methods herein described, and other optional devices including additional wire(s). Suitable packages include pouches, trays, tubes, boxes, and the like. The instructions may be printed on a separate package insert or may be printed in part or in whole on the packaging itself. The components of the kit within the package may be sterilized by conventional procedures.

Apparatus according to another aspect of the invention provides wire-deflection systems. Exemplary wire-deflection systems usually comprise a wire-deflecting catheter which includes a catheter body and a deflecting cannula. The catheter body has a proximal end, a distal end, and at least one lumen extending through at least a distal portion thereof. The lumen also has a distal opening and a lateral opening. In addition, the cannula has a proximal end, a distal end, and at least one lumen extending through a distal portion thereof. The distal portion of the cannula may also have a preformed, resilient curve. The cannula is slidably disposed within the lumen of the catheter body to assume (a) a straightened configuration when the cannula is proximally retracted within the catheter body lumen and (b) a curved configuration when the cannula is extended laterally through the lateral opening of the catheter body. In this way, the cannula can be selectively deflected through the intimal layer of the blood vessel back into the lumen of the blood vessel according to some of the preferable methods described herein. The system may further comprise a wire configured to pass through the cannula lumen. The wire may be a conventional guidewire or a modified wire having a sharpened distal tip intended particularly for penetrating the intimal layer of the blood vessel wall. Optionally, the wire may further comprise an imaging apparatus such as an ultrasonic imaging means. The catheter body may include a fluoroscopically visible marker near its distal end. The marker can be configured to permit visual determination of the rotational orientation of the distal end of the catheter body when viewed as a two-dimensional fluoroscopic image. The catheter body will usually be reinforced to enhance torsional rigidity, and may further comprise a distal nose cone wherein the distal and lateral openings are defined within the nose cone. The distal end of the cannula will usually be pre-formed in a smooth curve which may extend over an arc in the range from about 15 to 135 degrees, usually from about 45 to 90 degrees. The preformed curve may also have a radius in the range from approximately 0.5 mm to 15 mm, usually from approximately 2 mm to 10 mm. These and other objects and advantages of the invention will become more apparent upon further consideration of the entire specification and drawings. Additional aspects and details of the invention will become more apparent to those skilled in the relevant are upon review of the following detailed description of the invention set forth below.

BRIEF DESCRIPTION OF THE DRAWINGS

FIG. 3BB illustrates an alternate guidewire advancement step for the method of FIGS. 3A–3D.

FIGS. 8–9 are cross-sectional views of the distal end of a catheter similarly shown FIG. 7, illustrating an internal cannula in a retracted and advanced configuration, respectively.

DETAILED DESCRIPTION OF THE INVENTION

The present invention provides methods and apparatus for crossing a substantially or totally occluded blood vessel. Each of the disclosed embodiments may be considered individually or in combination with other variations and aspects of the invention. The methods and apparatus provided herein may be useful in coronary arteries and other blood vessels with or without assistance from imaging techniques from various regions within the body including areas within or adjacent to blood vessel walls. While the some aspects of the invention may be particularly applicable for the treatment of coronary artery disease, they are also useful and equally applicable in the treatment of other arteries and veins, and for other conditions including peripheral vascular diseases.

Figure 1:
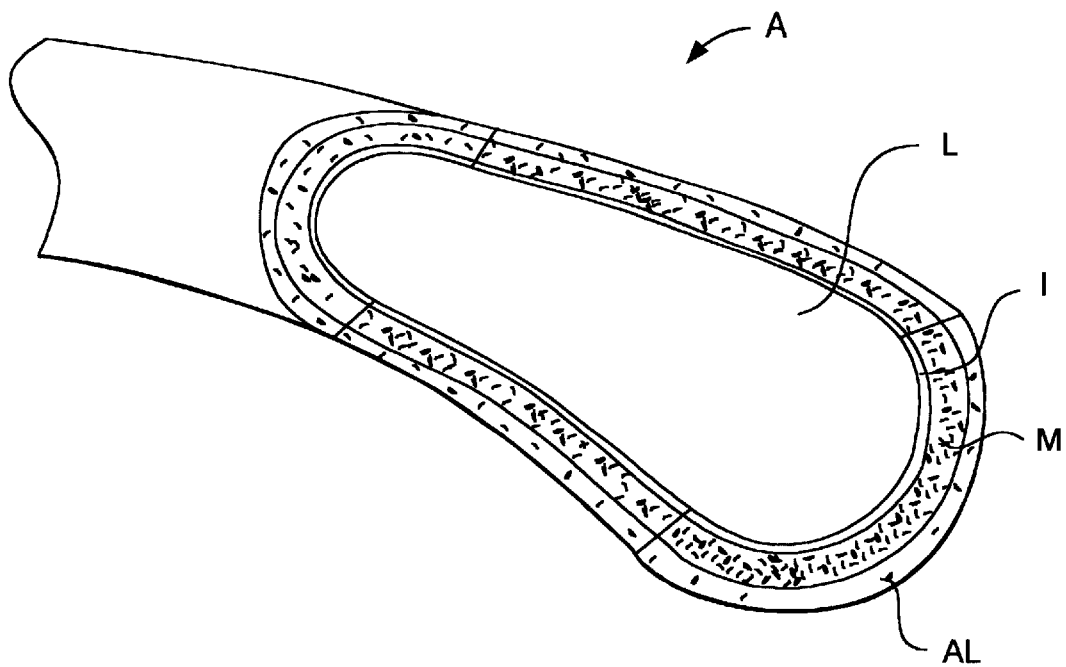
FIG. 1 is a schematic illustration of a coronary artery showing the intimal layer, the medial layer, and the adventitial layer.

As shown in FIG. 1, for example, a relatively normal non-diseased artery (A) generally comprises an arterial wall formed with a number of distinct layers. An innermost layer may be referred to herein as the intimal layer (I) which includes the endothelium, the subendothelial layer, and the internal elastic lamina. A medial layer (M) of the blood vessel is located concentrically outward from the intimal layer (I), and within another layer known as the adventitial layer (AL) which may be considered the relatively outermost layer. Beyond the adventitial layer (AL) generally lies surrounding extravascular tissue. As used hereinafter, the region between the intimal layer (I) and the adventitial layer (AL), generally including the medial layer (M), will be referred to as the subintimal space. It is generally the subintimal space through which the wires, deflecting catheters, and other catheters of the invention, will pass at least in part when crossing a total of substantially occluded blood vessel. The guidewires and deflecting catheters described herein may be formed of appropriate dimensions for placement and travel within these regions of the blood vessel wall. For most applications described herein, it is most often preferable to travel within the layers of the blood vessel wall, and across the inner wall of the blood vessel into the vascular lumen, without penetrating the outer wall region which would present additional safety concerns to a patient. These methods and apparatus may be of course directed to any region formed between other layers of a blood vessel wall other than those particularly described above.

Figure 2:
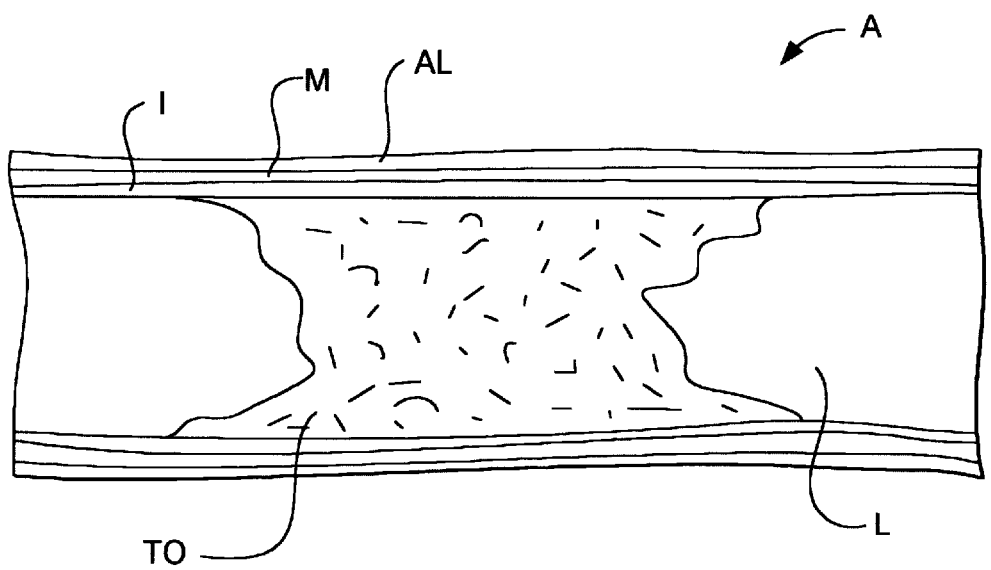
FIG. 2 is a schematic illustrations of a total occlusion within the coronary artery of FIG. 1, shown in full section.

FIG. 2 provides an illustration of a total occlusion (TO) within an artery (A) such as a coronary artery. The total occlusion (TO) may comprise atheroma, plaque, thrombus, and/or other occluding materials normally associated with cardiovascular disease. A "total" occlusion may be described to include an obstruction consisting of occluding material that substantially blocks or occludes the entire lumen (L) of the artery (A), or any other blood vessel, so that blood flow through the vessel is substantially stopped or hindered. The invention may be particularly applicable for patients with a totally occluded artery that is not immediately life threatening since the tissue distal to the occlusion may receive oxygenated blood from collateral arteries and circulation. However, the blood supply is usually insufficient, and it is often desirable to treat the occlusion by an intravascular intervention, such as angioplasty, atherectomy, stenting, or the like, to restore blood flow through the affected vessel. Before most of these and other interventional procedures can be performed, a guidewire is generally placed across the occlusion. When a vascular occlusion prevents the placement of a guidewire across the obstruction, one aspect of the invention thus provides various methods for crossing the substantially or totally occluded blood vessel. A guidewire may be initially selected with a deflectable distal tip configured for placement within or in between the layers of a blood vessel wall. A longitudinal dissection plane may be created within the blood vessel wall by inserting the guidewire into blood vessel wall from within the blood vessel lumen at a proximal location relative to a vascular occlusion. A channel may be formed in between the layers of and along the blood vessel wall by advancing the guidewire in a relatively distal direction along the blood vessel wall. Various imaging procedures may be performed to identify the relative location of the occlusion and blood vessel lumen. For example, imaging of a coronary may be accomplished from a position in a vein adjacent to the coronary artery. When the relative positioning of the guidewire and the occlusion are verified, the distal tip of the guidewire may be selectively deflected at a relatively distal location relative to the proximal location back into the blood vessel lumen. Upon placement of a guidewire across the vascular occlusion, interventional or diagnostic procedures may be subsequently performed over the guidewire, and more specifically, the interventional or diagnostic catheter may be advanced over the deflected guidewire from a position relatively proximal to the occlusion, through the channel, and back into the blood vessel lumen. The distal tip of the guidewire may be also deflected by providing the guidewire tip with a resilient curved end, and distally advancing the guidewire from a constraining lumen into the blood vessel lumen.

Figure 3A:
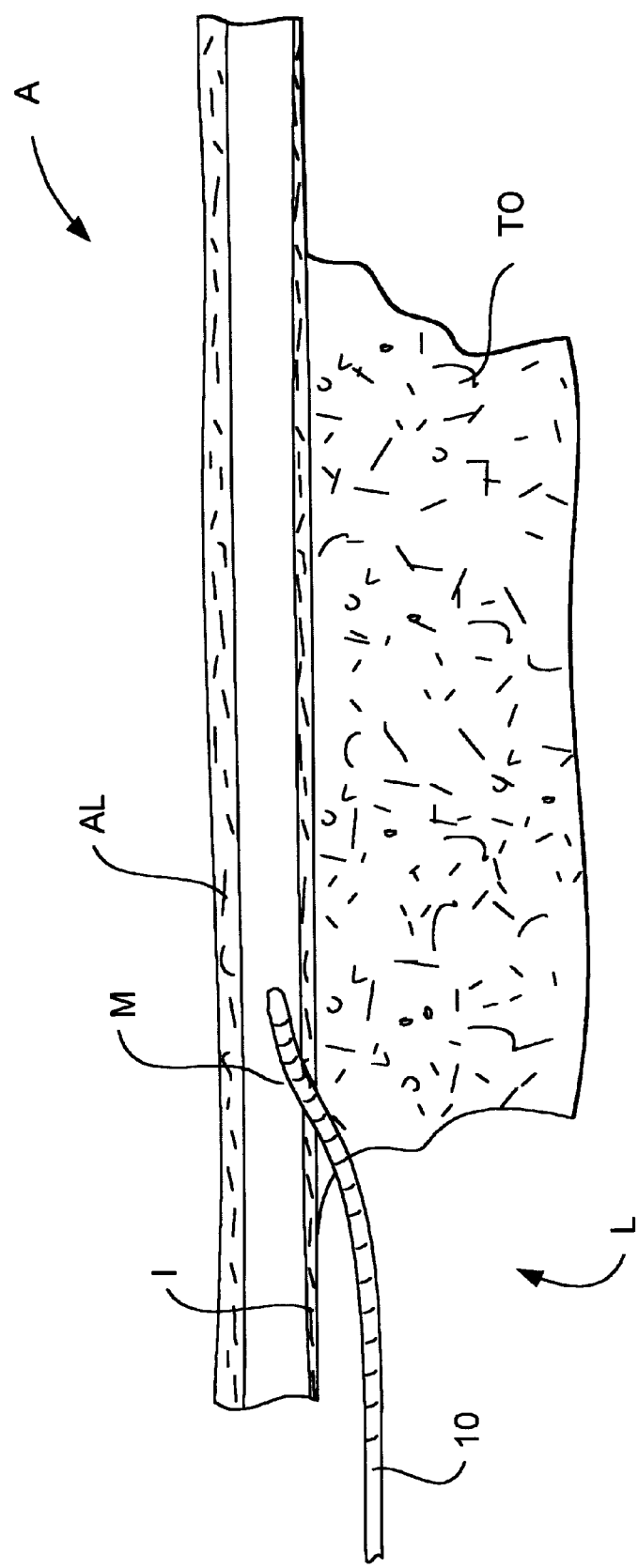
FIGS. 3A–3D illustrate the method of the present invention for crossing a total occlusion with a wire using a deflecting catheter.
Figure 3B:
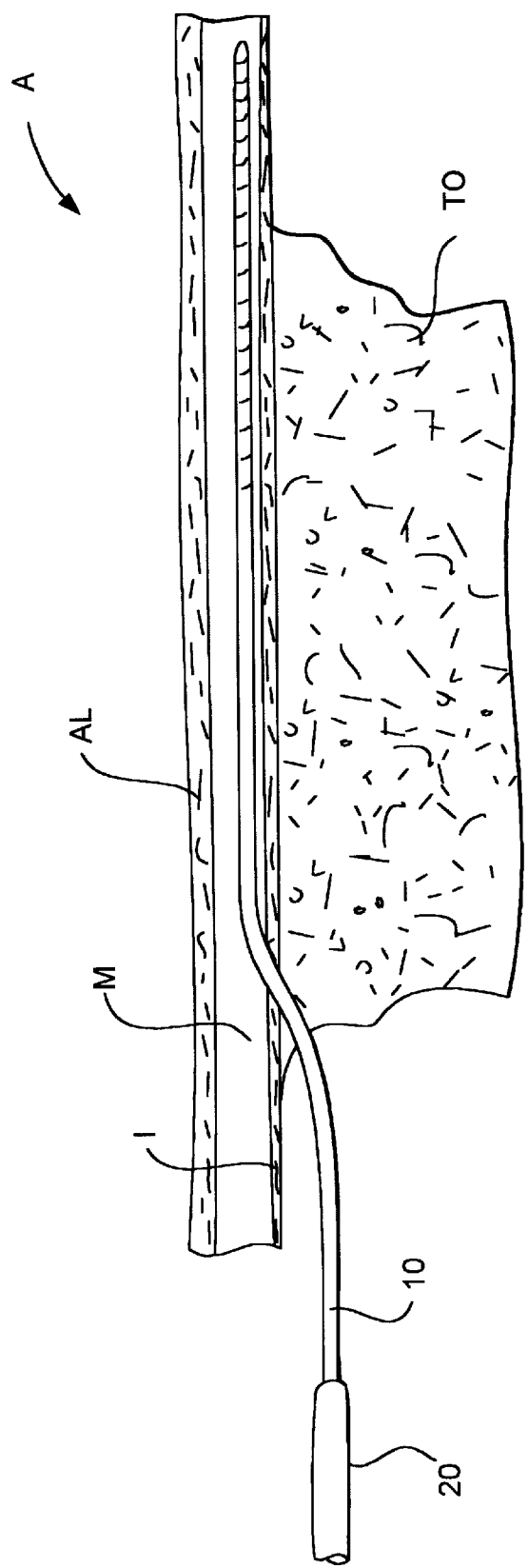
Figure 3B:
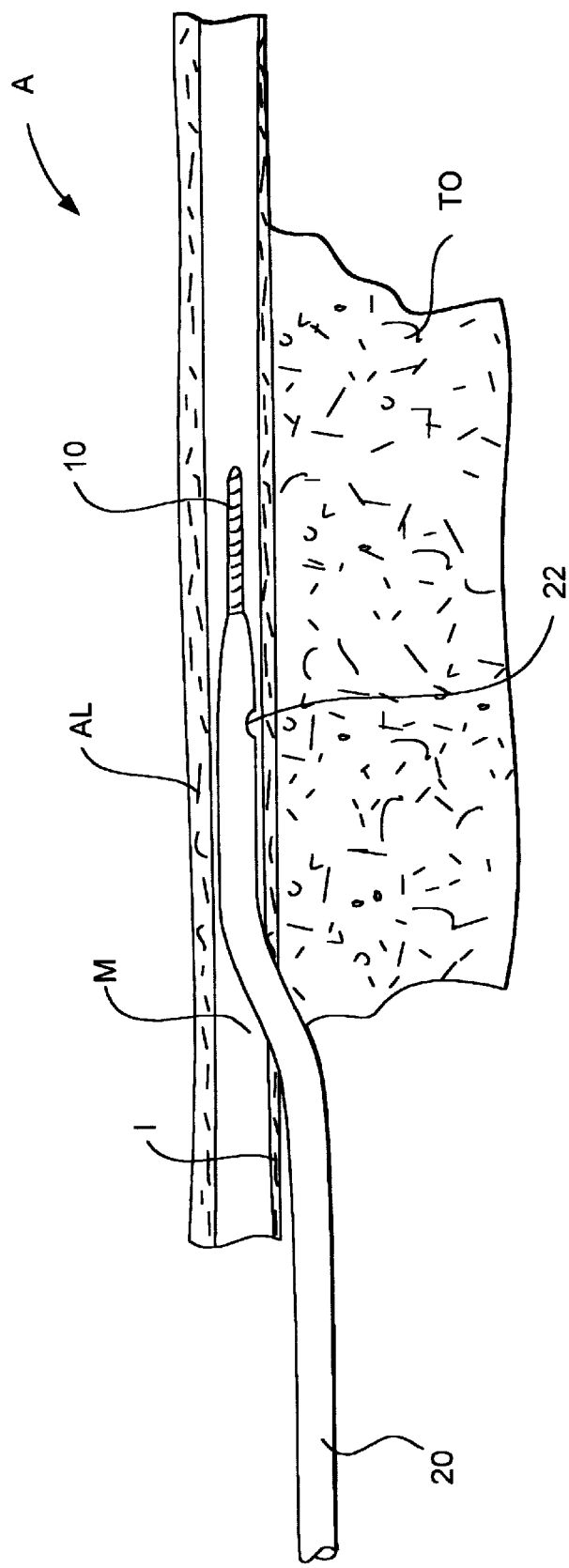

Another aspect of the present invention provides methods of crossing a vascular occlusion by controllably directing a deflectable wire into and through a blood vessel wall as described in FIGS. 3A–D. For purposes of illustration, this series of figures may represent an upper portion of an occluded artery (A) as shown in FIG. 2. A wire 10 may be advanced through the lumen (L) of an artery (A), as shown in FIG. 3A, until it encounters a total occlusion (TO). At that time, it may be possible for the wire 10 to be distally advanced through the occlusion without deflecting into the blood vessel wall. Should that occur, subsequent repositioning or redirecting of the guidewire according to the methods of the present invention may be performed, but may not be necessary. More usually, however, the wire 10 is not able to traverse a substantial occlusion by distally advancing the wire through the obstruction. The wire 10 may likely advance into the subintimal space within the medial layer (M) as shown in FIG. 3A. Of course, the wire 10 may also travel into or around at least a portion of the total occlusion (TO) before or while it is distally advanced. The intimal layer (I) and the adventitial layer (AL) together may define a tissue plane through which the wire 10 will naturally pass as the wire is pushed distally from its proximal end. The wire 10 may continue to advance further until its tip passes beyond the distal end of the total occlusion (TO) as shown in FIG. 3B. The tip could axially or distally advance well beyond the total occlusion to a desired location or until advancement is ceased. Although the guidewire 10 in FIG. 3B is shown as being advanced without support, in some instances the guidewire may however encounter significant resistance as it enters and/or passes through the space between the intimal layer (1) and the adventitial layer (AL), or any other layers within a blood vessel wall. When resistance is encountered, the deflection catheter 20 may be used to axially support and enhance the "pushability" of the guidewire 10 by advancing the catheter over the proximal end of the guidewire to a location just proximal of the distal tip of the guidewire as shown in FIG. 3BB. The guidewire 10 and catheter 20 may then be advanced together or sequentially, e.g. advancing the guidewire a short distance followed by advancing the catheter, as needed to direct the distal tip of the guidewire, or a lateral port 22 formed in the catheter, to a relatively distal location which may be proximal to or past the total occlusion (TO).

Figure 3C:
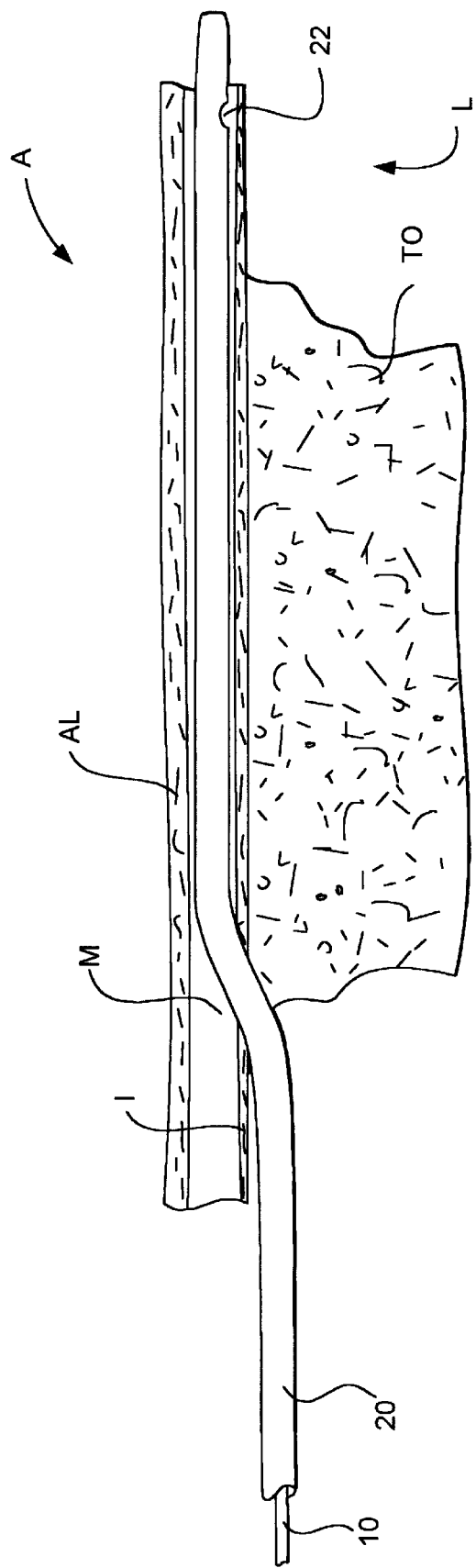
Figure 3D:
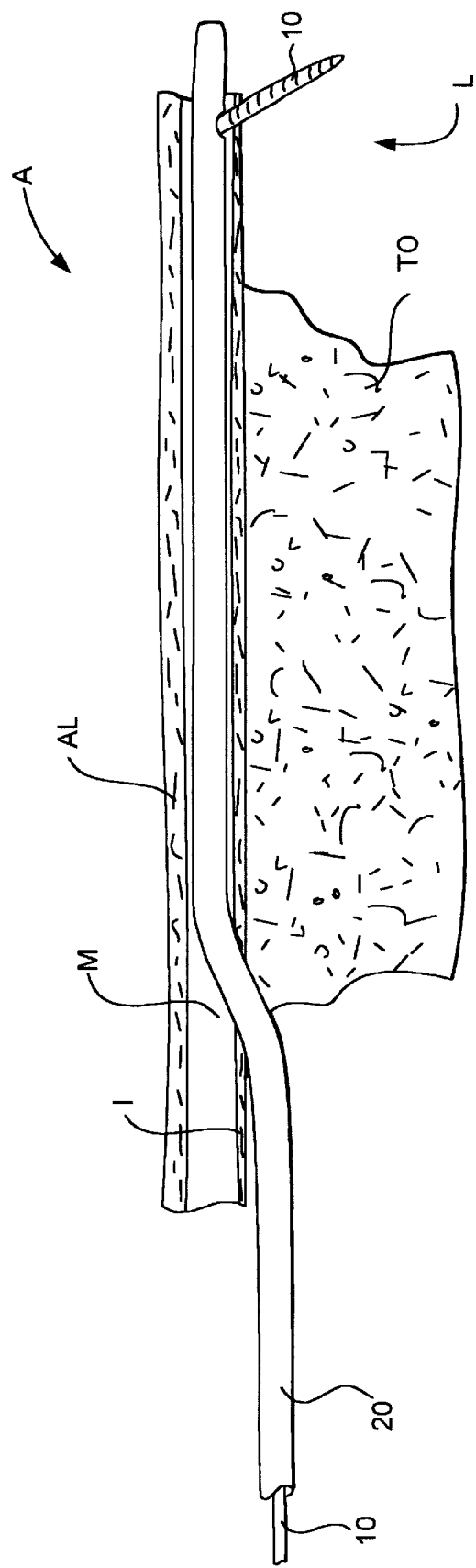

When the distal tip of the guidewire 10 is advanced to a desired location without additional support from the deflecting catheter 20, and is positioned beyond the total occlusion (TO), the deflecting catheter may be advanced over the wire 10 by coaxial introduction over the proximal end of the wire until it approaches the total occlusion as shown in FIG. 3B. The deflecting catheter 20 may be further advanced over the wire 10 until its distal tip also extends beyond the total occlusion (TO) as illustrated in FIG. 3C. The deflecting catheter 20 includes a redirecting Mechanism for laterally deflecting the wire 10 so that it may pass back in a radially inward direction through the intimal layer (I) back into the blood vessel lumen (L) when the catheter is sequentially moved in a relatively distal direction, and a relatively proximal direction thereafter. Rather than advancing and withdrawing the catheter 20 in a proximal direction, the guidewire 10 may be withdrawn and advanced in a distal direction to be deflected. The deflection mechanism may be selected from various redirecting devices an may take a variety of forms as described below. For example, as shown in FIG. 3C, a lateral port 22 is provided in the deflecting catheter 20. The wire 10 may be retracted so that its distal tip lies proximally of the lateral port 22, and may then be advanced distally so that the wire passes laterally outwardly through the port and back into the blood vessel lumen as shown in FIG. 3D. Various deflecting catheters and apparatus described herein for directing and redirecting a guidewire within a blood vessel wall may be selected to perform these procedures in accordance with the concepts of the invention.

The location and orientation of the deflecting catheter and wire assembly may be monitored in various ways to carry out the described methods for crossing a substantially occluded blood vessel. In particular, it may be desirable to assure that the distal tip of the wire 10 and the port 22 or other deflecting mechanism of the deflecting catheter 20 is properly positioned beyond the total occlusion (TO) without being advanced excessively beyond the end of the total occlusion. Typically, it may be desirable to position the deflecting mechanism at a range from approximately 0 to 2 cm beyond the distal end of the total occlusion (TO), and preferably from 0 to 0.5 cm. As discussed above, the positioning of the relative components may in some instances be performed using conventional fluoroscopic imaging. For example, it may be sufficient to provide suitable radiopaque markers on the wire and/or on the deflecting mechanism of the deflecting catheter 20 to permit visual positioning and rotational orientation of the tip via fluoroscopy. Often, however, it may be desirable to provide ultrasonic or other imaging at or near the total occlusion. A wire 10 may be thus provided with ultrasonic imaging so that the presence and the absence of the occluding material may be detected as the wire is advanced passed the total occlusion (TO). Alternatively, the deflecting catheter 20 may be provided with ultrasonic imaging in the form of a phased array located near the distal tip (not shown). Ultrasonic imaging guidewires are known to those skilled in the relevant field and are described in the patent literature as in U.S. Pat. No. 5,095,911, the full disclosure of which is incorporated herein by reference. In yet another alternative, an imaging guidewire may be advanced to the region of the total occlusion (TO) in a direction opposite to that of the wire 10 and catheter 20. In this way, the imaging guidewire need not advance through the total occlusion, but could still detect advancement of the catheter and/or guidewire, particularly if ultrasonically opaque components were provided on either or both of the catheter and wire. In yet another alternative, an ultrasonic imaging catheter or guidewire could be positioned in a vein adjacent to the arterial occlusion site, allowing imaging of the entire occluded region while the guidewire is advanced there through. Other imaging modalities may be employed including apparatus such as optical coherence tomography (OCT) (see U.S. Pat. Nos. 5,321,501; 5,459,570; 5,383,467; and 5,439,000), fluorescence imaging (see U.S. Pat. Nos. 4,718,417; and 5,106,387), and Raman spectroscopy (WO 92/18008).

Another desirable feature of the methods prescribed by the present invention includes the rotational positioning of the deflecting catheter 20. It will be appreciated that the direction of deflection is usually selective, and it will be therefore desirable to aim the deflecting mechanism from the subintimal space back toward the arterial or blood vessel lumen (L). If the catheter 22 is provided with ultrasonic imaging, such imaging can be used for rotationally positioning the distal tip of the catheter. The catheter may be rotationally rigid so that rotation of its proximal end may position the distal end of the device in a substantially similar manner or orientation. By detecting the presence or relative location of the blood vessel lumen (L), the deflecting port 22 or other deflecting mechanism can be properly positioned. In an alternative embodiment, as further illustrated below, a catheter may include a rotationally specific fluoroscopic marker, preferably towards its distal end region. The marker may be such that by observing the two-dimensional image of the marker by fluoroscopic imaging, the rotational direction of the catheter tip can be determined.

Figure 4:
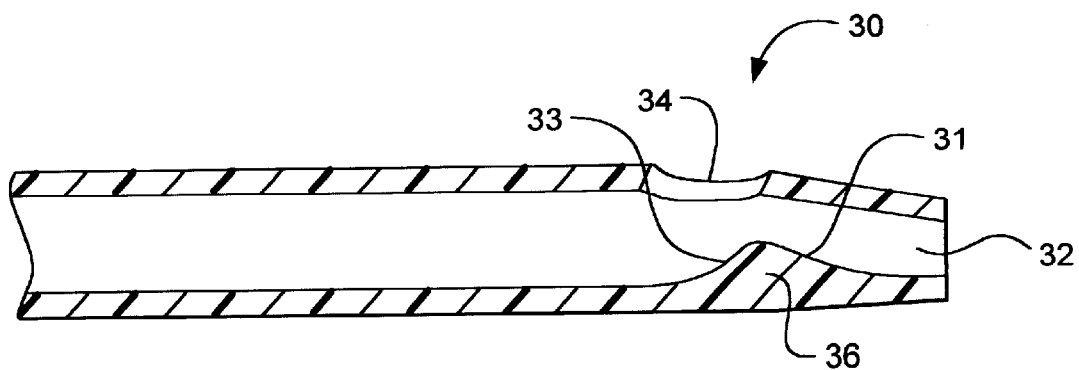
FIG. 4 illustrates the distal end of a deflecting catheter formed in accordance with the invention.
Figure 5:
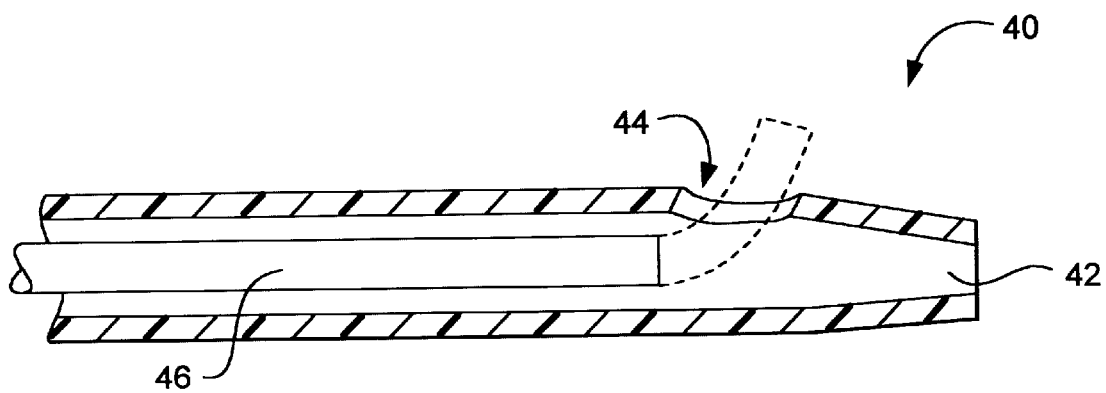
FIG. 5 illustrates the distal end of another deflecting catheter useful in the methods of the present invention.
Figure 6:
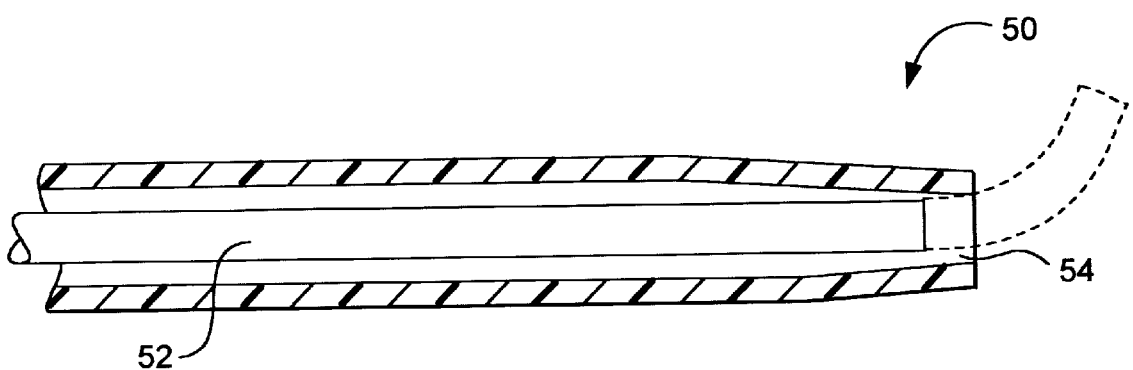
FIG. 6 illustrates the distal end of another embodiment of the invention that provides a deflecting catheter.

FIGS. 4–6 illustrate several exemplary deflecting mechanisms for the catheters provided by the present invention. As shown in FIG. 4, the distal end of a catheter 30 may have a distal port 32, a lateral port 34, and a passive deflecting mechanism 36. The passive deflecting mechanism may include a first and a second inclined guiding surface 31 and 33. The first inclined guiding surface 31 may be formed in a relatively distal position, and may be formed to direct the proximal end of a guidewire (not shown) into the main lumen of the catheter from the distal port 32. The guidewire may be thereafter displaced relatively proximal to the catheter so that the distal end of the guidewire approaches and passes the passive deflecting mechanism 36 in a relatively proximal direction. The second inclined guiding surface 33, which may be formed in a relatively proximal position, may thereafter direct the distal end of the guidewire in a deflected position through the lateral port 34 when the guidewire engages the second surface 33 upon subsequent distal advancement of the guidewire. For example, the catheter 30 may be advanced over the proximal end of a wire so that the wire passes over the distal surface 31 of the deflecting mechanism 36, and back into the main lumen of the catheter 30. In general, the catheter 30 is advanced distally in an over the wire manner relative to the guidewire when the distal tip of the guidewire is believed to lie relatively distal to a vascular occlusion within a blood vessel wall. The catheter 30 may be advanced over the wire so the distal tip of the catheter enters the subintimal space and approaches the distal end of the guidewire. By retracting the distal end of the wire within the lumen of catheter 30 so that its distal tip is proximal to the deflecting mechanism 36, subsequent distal advancement of the wire thereafter will engage the proximal surface 33 of the deflecting mechanism and cause the wire to be deflected laterally through lateral port 34.

Several examples of active deflecting mechanisms for redirecting a guidewire are illustrated in FIGS. 5–6. A catheter 40 may be formed with a distal port 42 and a lateral port 44 as shown in FIG. 5. Rather than a passive deflecting mechanism, the catheter 40 may include an axially translatable cannula 46 having a resilient, pre-formed distal tip which may be advanced through port 44 as shown with broken lines. The cannula 46 may include a lumen which provides a guide path for the wire (not shown) when the cannula is placed in a deflected or non-deflected position. Meanwhile, the catheter 50 illustrated in FIG. 6 is similar to the catheter 40 in FIG. 5, except that no lateral port is provided. Instead, a cannula 52 having a preformed distal end may be advanced and retracted out of a distal port 54 of the catheter 50 so that its distal end can assume a laterally deflected shape as shown with broken lines. It will be appreciated that these embodiments are intended to be exemplary only, and a wide variety of other passive and active deflecting mechanisms may be provided on deflecting catheters for use in accordance with the concepts of the present invention.

Figure 7:
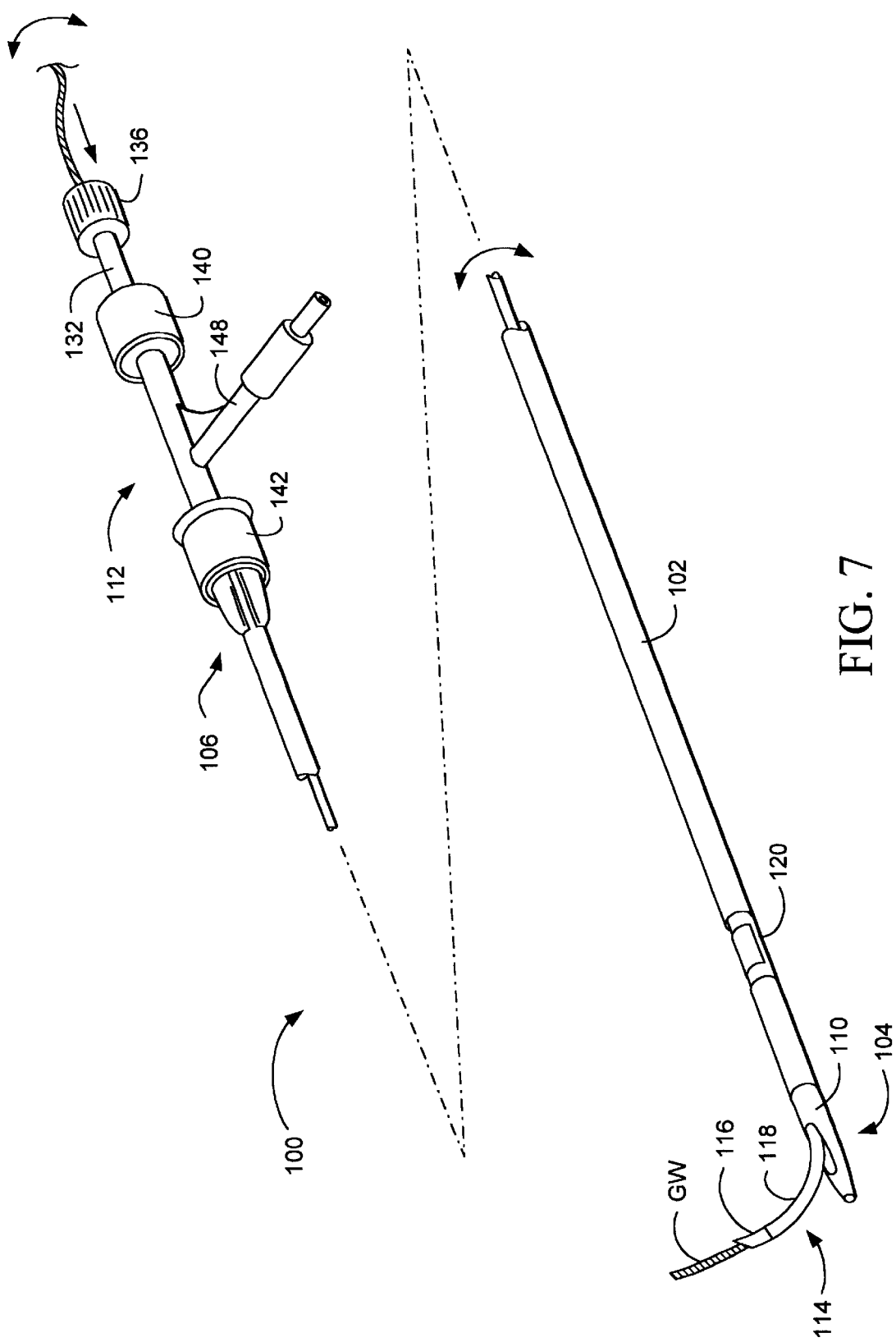
FIG. 7 illustrates a wire-deflecting catheter system formed in accordance with the present invention.
Figure 10:
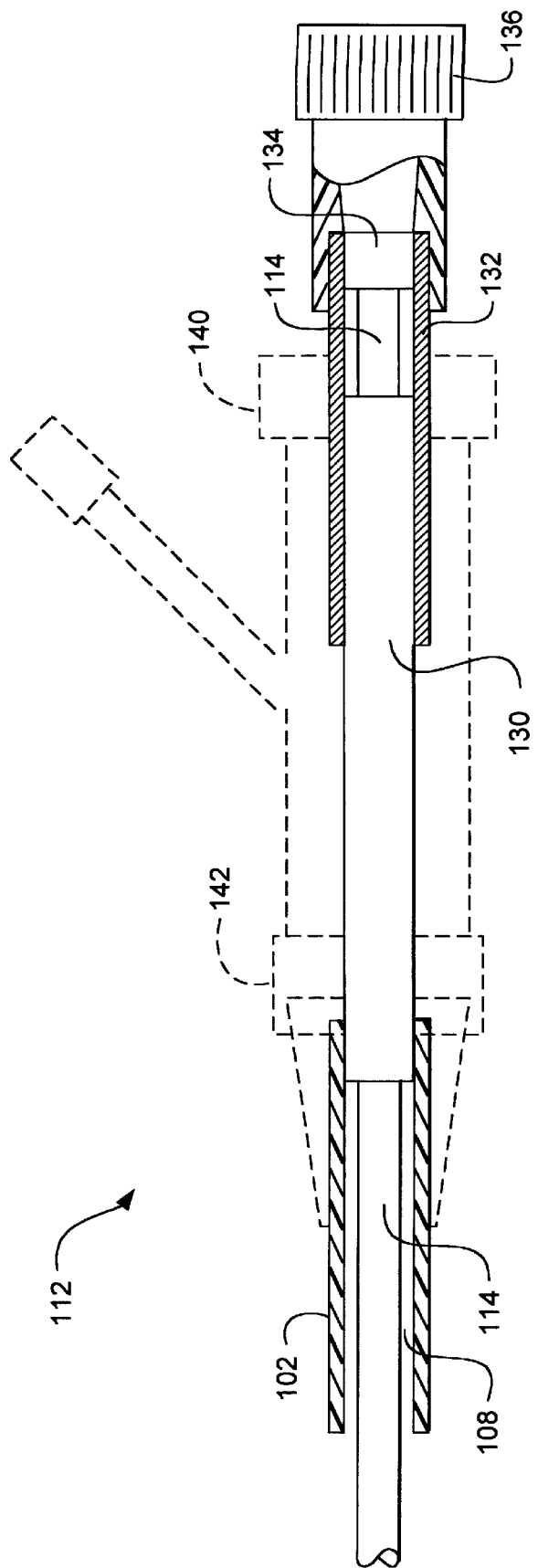
FIG. 10 is a schematic illustration of a proximal hub of a catheter for deflecting and directing a guidewire in accordance with the methods and apparatus of the invention.

Referring now to FIGS. 7–10, an exemplary deflecting catheter 100 formed in accordance with the principles of the present invention is described in detail according to relative catheter sections. As shown generally in FIG. 7, the deflecting catheter 100 comprises a catheter body 102 having a distal end 104 and a proximal end 106. Catheter body 102 includes a single lumen 108, as shown in FIGS. 8–10, and a deflecting housing 110 secured to the distal end 104 thereof. An actuator hub 112 may be secured to the proximal end 106 of catheter body 102, and an axially translatable cannula may be disposed within lumen 108. The cannula 114 may be formed with a sharpened tip 116, typically formed from a metal, hard plastic, composite, or the like, optimally being radiopaque. Alternatively or additionally, it may be desirable to provide at least one separate radiopaque marker or the cannula at or near its distal end to facilitate visualization under fluoroscopic imaging. A distal length 118 of the cannula 114 can be pre-formed with a curved shaped as shown in FIGS. 7 and 9. A rotationally specific radiopaque marker 120 may be mounted near the distal end of catheter body 102. As illustrated, the marker has a generally U-shaped or otherwise directional configuration so that the rotational position of the distal end of the catheter body 102 will be apparent when the marker is observed in a two-dimensional fluoroscopic image.

The catheter 100 provides lateral deflection to the distal tip of the cannula 114 which extends beyond the catheter body 102 through a lateral opening 122 in the deflector housing 110 as shown in FIGS. 7–9. The deflector housing 110 also includes a distal port 124 to permit introduction of the catheter 100 over the proximal end of a guidewire GW as illustrated in FIG. 8 with broken lines. The guidewire GW passes through the distal port 124, and into the distal end of the cannula 114, and may travel through a lumen of cannula all the way to the proximal end of the catheter 100. The distal length 118 of cannula 114 may be straightened and deflected by axially retracting and advancing the cannula between the configuration shown in FIG. 8 and FIG. 9, respectively. The cannula 114 may be formed with an appropriate diameter or cross-section to permit its passage through the layers of blood vessel wall and may range from approximately 1 F to 4 F. The cannula 114 may be formed of from a wide range of biocompatible materials such as polyimide, PEEK or nitinol. Similarly, the guidewire GW should also have dimensions that allow its travel through the relatively thin layers of a blood vessel wall, and may range from approximately 0.010 in. to 0.038 in. The GW may be a conventional intravascular guidewire and may be formed of a variety of materials including stainless steel and nitinol. The distal tip of the cannula 114 may include a tissue penetrating element 116 to assist the cannula in re-entering the lumen of a blood vessel from within the wall region. The cannula 114 should provide sufficient stiffness in order to transmit enough force to penetrate the inner blood vessel wall but not enough so as traverse the outer vessel wall to regions outside of the blood vessel. The tissue penetrating element 116 may be formed of gold-plated stainless steel, platinum, or platinum iridium alloy or other radiopaque materials.

FIG. 10 provides an illustration of an actuator hub 112 comprising a pair of coaxial, telescoping tubes 130 and 132. The outer telescoping tube 132 may be connected to a proximal end of cannula 114, typically by an adhesive 134 or any other connective material. A proximal fitting 136 is further attached to the proximal end of the outer telescoping tube 132 so that the assembly of the cannula 114, the tube 132, and the fitting 136 may move together as a unit through the hemostatic fitting 140 at the proximal end of the hub 112. The hub 112 may further include a rotational fitting 142 which permits the catheter body 102 to be rotated relative to the hub body. The cannula 114 and catheter body 102 may be rotationally coupled or "keyed" together to limit or prevent relative rotation, typically by keying within the hub and/or near the distal end, so that rotation of the catheter body causes a like rotation of the cannula as the catheter is rotationally positioned within a blood vessel. A side branch 148 may be provided on hub 112 to permit perfusion and/or infusion through the lumen 108 of catheter 102.

Figure 11A:
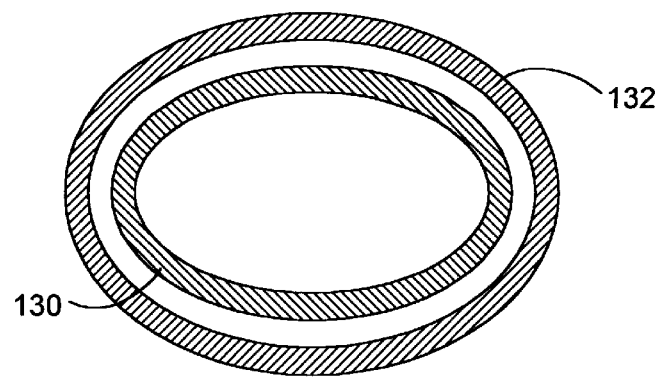
FIGS. 11A–11B illustrate variations for rotationally keying the proximal end of catheter shafts.
Figure 11B:
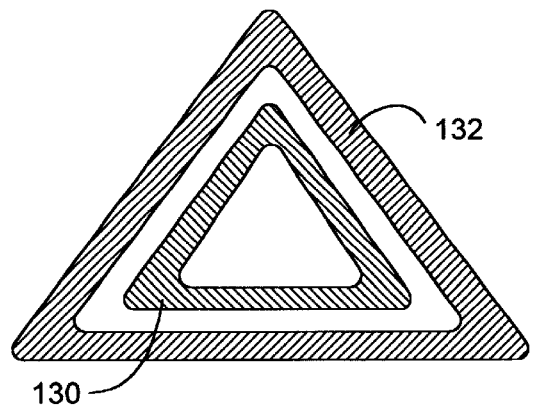
Figure 12:
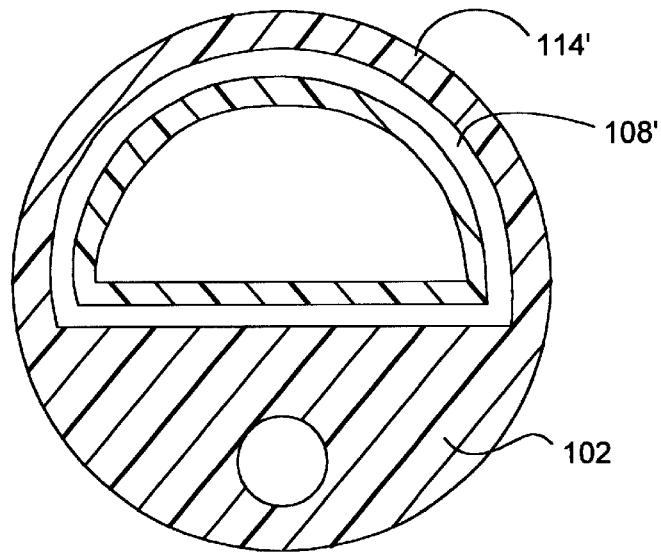
FIG. 12 illustrates variations for rotationally keying the distal end of a catheter.

Keying at the proximal end of the catheter 100 can be achieved in a variety of ways. For example, the telescoping tubes 130 and 132 can be provided with asymmetric, mating peripheral geometries, such as oval cross-sections shown in FIG. 11A or triangular cross-sections shown in FIG. 11B. Keying at the distal end can also be achieved in a number of ways, such as providing-the catheter body 102 with an asymmetric lumen 108' and the cannula 114' with a mating cross-section, e.g. a D-shaped cross-section as illustrated in FIG. 12. The ability to limit relative rotation of the cannula 114 within the catheter body 102 is advantageous since it may ensure that the curved distal length 118 is properly oriented (usually directed radially outwardly) when the tip 116 emerges through the opening 122. In use, the catheter 100 may be advanced over guidewire GW while the cannula 114 is retracted as shown in FIG. 8. Once the catheter is properly positioned, the cannula 114 may be distally advanced as shown in FIGS. 7 and 9. Distal advancement may be achieved by forwardly advancing the sleeve 132 in the hub 112 relative to the remainder of the hub so that the cannulas move forwardly within the lumen 108 of the catheter body 102. Prior to advancing the cannula, the port 122 may be properly positioned so that it is directed toward the blood vessel lumen by rotating catheter body 102, typically using the rotational hub 142. Conveniently, the physician may observe the marker 120 so that the lateral port 122 can be directed in the proper radially inward direction. After the cannula is advanced into the blood vessel, the guidewire GW may then be advanced distally into the lumen, the cannula 114 may be withdrawn proximally, and the entire catheter assembly may be then withdrawn from over the guidewire leaving the guidewire in place for introduction of other interventional and/or diagnostic catheters.

Figure 13A:
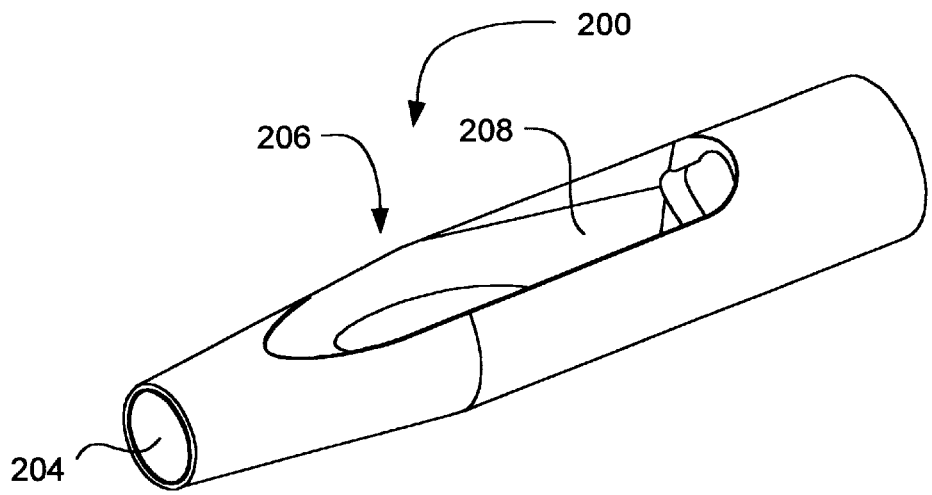
FIGS. 13A–C provide illustrations of a nosecone for a guidewire deflection catheter system formed in accordance with the invention.
Figure 13B:
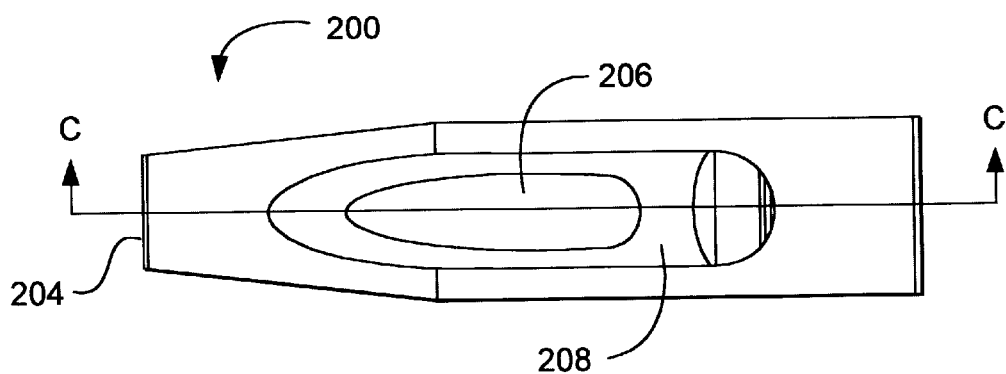
Figure 13C:
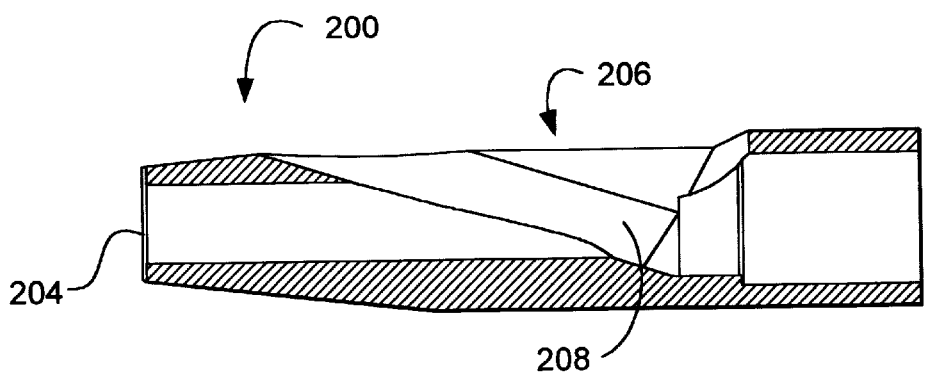

The deflection of a guidewire and/or cannula from within a vascular wall into the blood vessel lumen may be achieved by numerous deflecting mechanisms as described herein. For example, as shown in FIGS. 13A–C, a guidewire deflection system may be formed with a deflection nosecone assembly attached to the distal end of a catheter body. The nosecone assembly may be approximately 0.25 in. in length, and may of course vary in shape and dimensions according to particular applications. The catheter body (not shown) may further include a proximal portion, a longitudinal axis, and at least one lumen extending along at least a distal end portion thereof. As shown in FIG. 13A, a nosecone 200 may be formed with a distal opening 204, a relatively proximal and spaced apart lateral opening 206, and an inclined surface 208 adjacent to the lateral opening. The distal opening 204 of the nosecone 200 may have a substantially circular cross-section ranging from approximately 2 F to 6 F. The lateral opening 206 may be configured with an oblong or elliptical cross-section with a relatively lateral diameter of about 0.014–0.050 in., and a relatively longitudinal diameter of about 0.050–0.200 in. as shown in FIG. 13B. The distal opening 204 and the lateral opening 206 may be spaced apart approximately 2–5 mm, and preferably about 3 mm, or at other various distances along the nosecone 200, and may be both in communication with the catheter body lumen as shown in FIG. 13C. The lateral opening 206 and adjacent inclined surface 208 may receive a cannula passing therethrough from the catheter body lumen. In particular, the cannula (not shown) may have an external cannula surface that is configured and sized for slidable movement through the lateral opening 206 specifically. The cannula may be formed with at least one passageway extending through at least a distal portion thereof The distal end of the cannula may be configured to communicate with the inclined surface 208 adjacent to the lateral opening so as to deflect the cannula away from the longitudinal axis of the catheter body when the cannula is advanced in a relatively distal direction. Additionally, the distal portion of the cannula may have a preformed shape resilient curve, and may be slidably positioned within the lumen of the catheter body. The distal cannula portion may have a relatively axially aligned configuration with the lumen when the cannula is positioned within the catheter body, and may have a relatively curved configuration with the lumen when the cannula travels along the inclined surface 208 and through the lateral opening 206 of the catheter body when the cannula is distally advanced through the lumen within the catheter body. The pre-formed shape resilient curve at the distal portion of the cannula may extend over an arc in the range from approximately 15 to 135 degrees, and may have a radius in the range from approximately 1 mm to 20 mm. The cannula may also include a self-penetrating distal end that includes a sharpened distal tip. Moreover, the cannula may include a radiopaque or orientation marker substantially near its distal end or along any portion thereof.

The guidewire deflection system may further include a guidewire configured to pass through a passageway formed in the cannula. The guidewire (not shown) may be formed with an external guidewire surface that is configured or sized for slidable movement through the distal opening 204 of the nosecone 200, and may range from approximately 0.010–0.038 in. When the guidewire is initially placed within the layers of blood vessel wall along a selected dissection plane, the distal opening 204 of the nosecone 200 may receive the proximal end of the guidewire to permit its passage therethrough and along a longitudinal lumen formed within a cannula in the attached catheter body. The nosecone 200 may be tapered and formed with a substantially circular or elliptical cross-section, or may even have a wedge shaped cross-section or any other configuration that may facilitate passage in between the vessel layers along the selected dissection plane. Moreover, a hub (not shown) may be rotationally secured to the proximal end of the catheter body to controllably rotate the cannula and the catheter body (see generally FIG. 10). The hub may further include a controller connected to the cannula for controlling the slidable movement of the cannula within the catheter body (see generally FIG. 7). After the location and orientation of the distal tip of the guidewire is ascertained, the guidewire may be deflected into the blood vessel lumen by withdrawing the cannula and guidewire in a relatively proximal direction so at least the distal tip of the cannula is proximal to the lateral port 206 and the inclined surface 208. The cannula may be then advanced in a relatively distal direction so the tip of the cannula, which may be relatively sharpened, engages the inclined surface 208 adjacent to the lateral port 206. The guidewire may be advanced distally thereafter, and relatively lateral deflection of the guidewire is thus achieved by the deflection nosecone assembly. Additionally, the guidewire, cannula, or catheter body may also include means for imaging tissue surrounding the wire. The distal end of the catheter body may include a fluoroscopically visible marker substantially near its distal end to permit visual determination of the rotational orientation of the nosecone 200. The nosecone 200 may likewise have a variety of fluoroscopic markers.

Figure 14A:
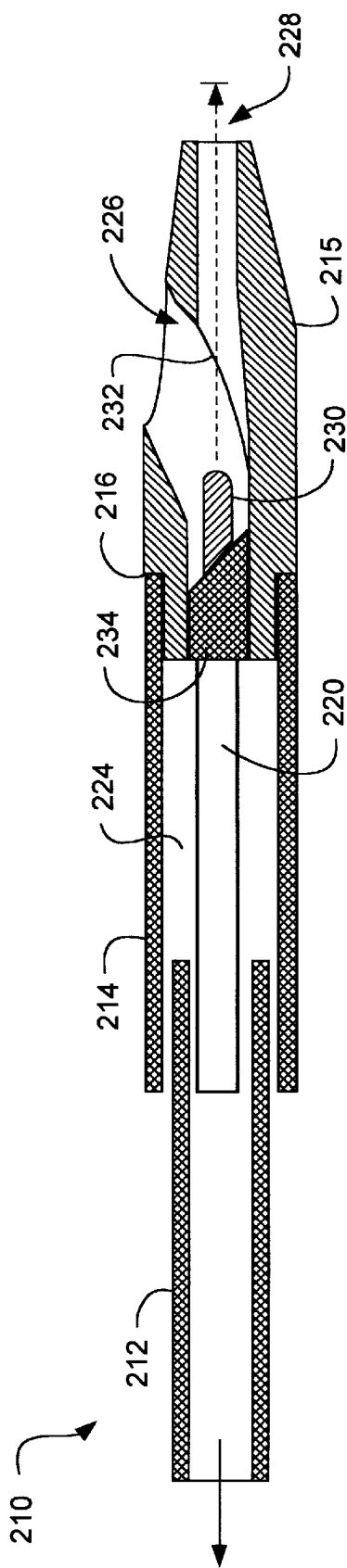
FIGS. 14A–B are cross-sectional side views of a nosecone connected to the distal end of a catheter shaft with an internally positioned cannula and guidewire.
Figure 14B:
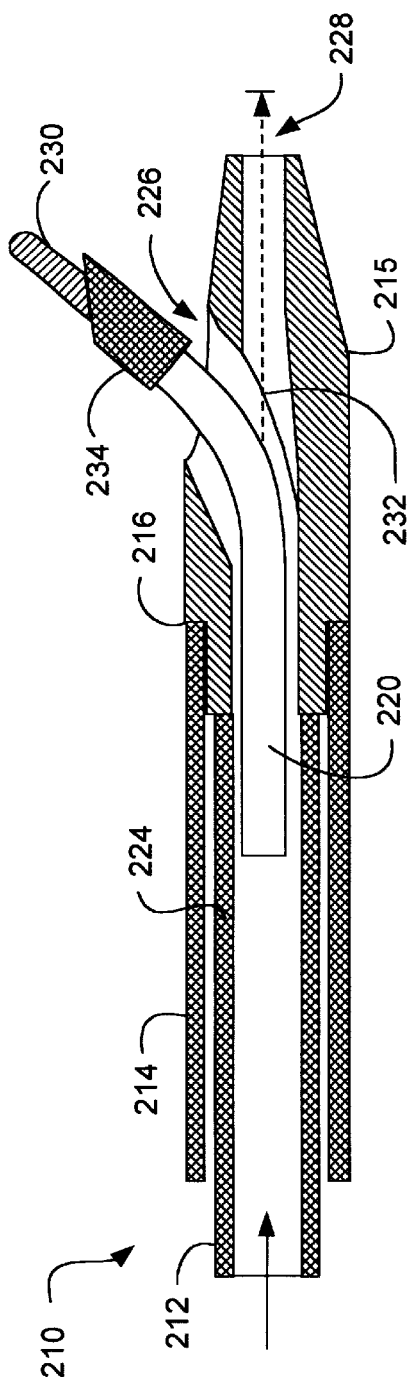
Figure 15A:
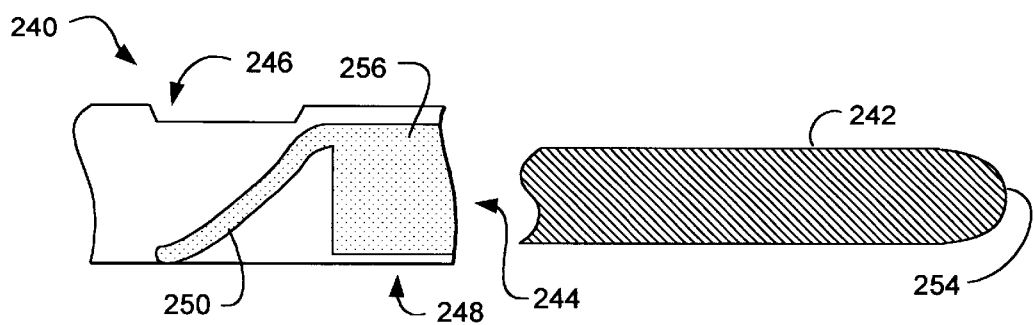
FIGS. 15A–E are simplified side views of a flapper mechanism positioned at the distal portion of a catheter that controllably deflects a guidewire through a distal end port and/or a lateral port.
Figure 15B:
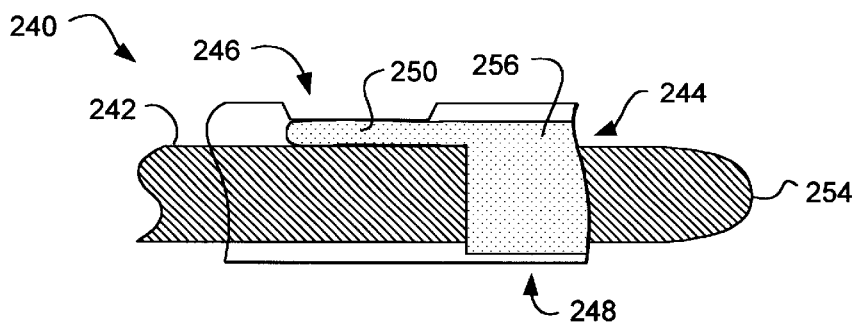
Figure 15C:
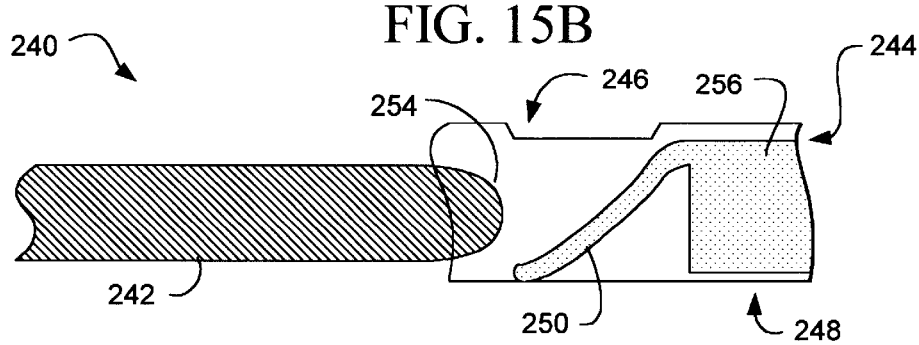
Figure 15D:
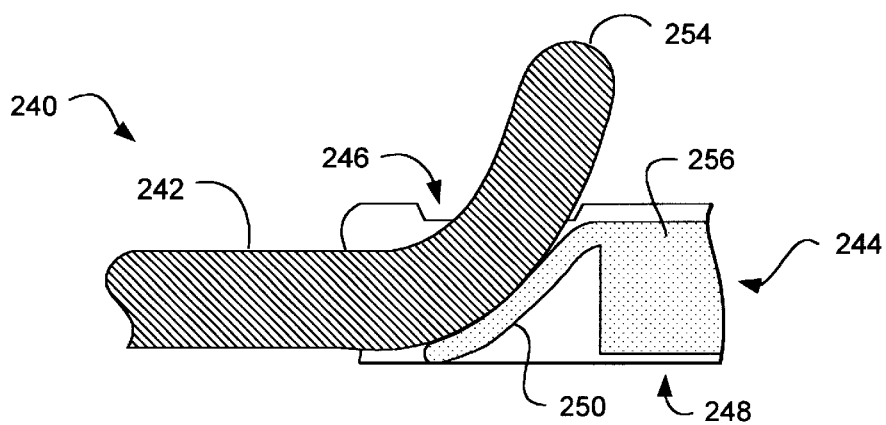
Figure 15E:
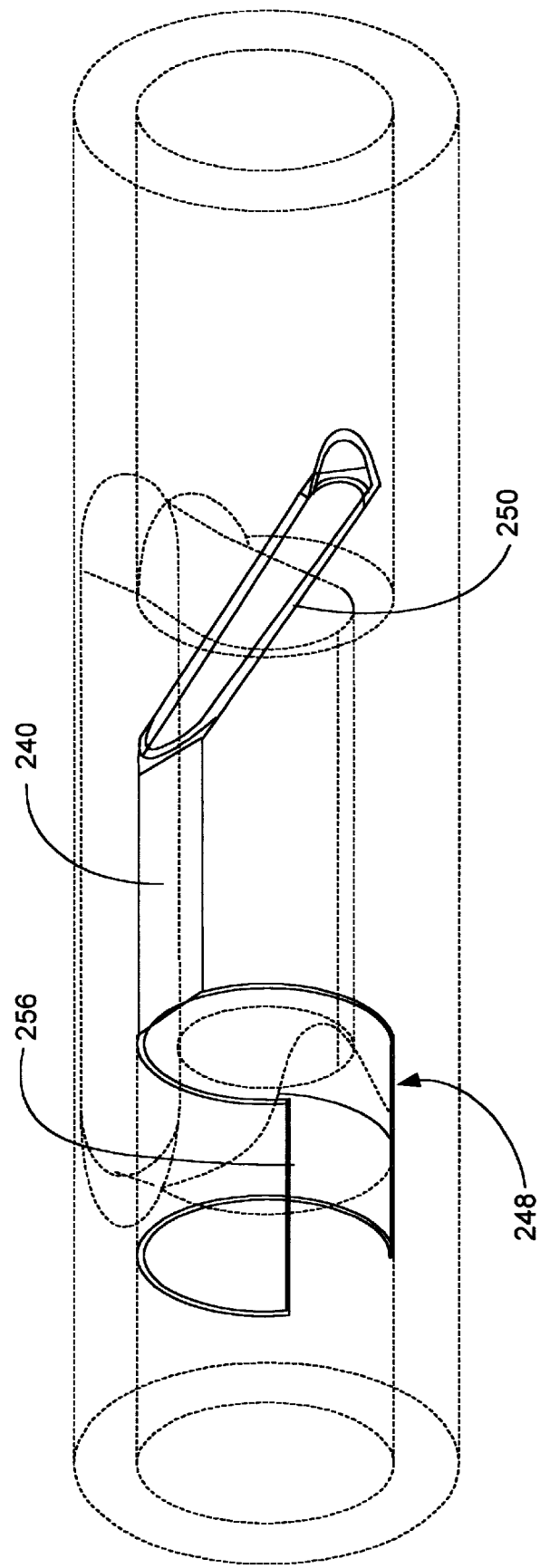

FIGS. 14A–B provide additional illustrations of an intravascular catheter that includes a guidewire deflection assembly 210. The catheter may be formed with a pair of relatively inner and outer shafts 212 and 214 that are coaxially positioned with respect to each other. A nosecone portion 215 may be connected to the distal end 216 of the outer catheter shaft 214 by known techniques in the art. Additionally, a cannula 220 may be positioned within the catheter that is formed with a guidewire passageway and an external cannula surface. The cannula 220 may be connected to the inner shaft 212, and may be slidably positioned within at least a portion of the longitudinal lumen 224 of the outer catheter shaft 214. The cannula 220 may not necessarily extend within the entire length of the catheter, and may be located external to the catheter along some relatively proximal portion. As shown in FIG. 14B, the distal end of the inner shaft 212 may come in contact with the proximal end of the nosecone 215 when advanced distally so as to controllably limit the extended length of the cannula 220. The external surface of the cannula 220 may be configured for selective passage of the cannula through a first or lateral port 226 but not through a second or distal port 228 formed in the nosecone 215. A guidewire 230 formed with an external surface may be thus configured for passage through the distal port 228 too, and may be slidably positioned within at least a portion of the cannula passageway. When the cannula 220 is positioned relatively coaxial within the catheter, the guidewire 230 within the cannula may be directed to enter or to exit the catheter through the distal port 228. The first port 226 in the nosecone 215 may have a first transverse cross-sectional area, and may be in communication with a longitudinal lumen 224 that is defined by the inner walls of the outer shaft 214. The second port 228 may also be in communication with the longitudinal lumen 224, wherein the second port is formed with a second transverse cross-sectional area. The first cross-sectional area may be relatively larger or smaller than the second cross-sectional area, and are preferably formed with different dimensions or configurations so selective passage of the cannula 220 may be achieved.

A variety of imaging and orientation markers may be also positioned along various portions of the guidewire 230, cannula 220 and/or catheter body. In particular, the nosecone 215 may include a radiopaque marker or imaging componentry that provides directional orientation of the distal portion of the catheter or the relative direction in which the lateral port 226 is facing. The nosecone 215 may include ports of various sizes, and may define a first port 226 as a substantially elliptical orifice and the second port 228 as a substantially circular orifice. The immediate area of nosecone 215 surrounding the first port 226 may define an inclined surface 232 for receiving a distal cannula tip section 234 that leads to the first port.

Additional guidewire deflecting mechanisms provided in accordance with the invention are shown in FIGS. 15–20. A flapper assembly 240, as shown in FIGS. 15A–E, may be positioned at the distal portion of a catheter to controllably deflect a guidewire 242. The flapper assembly 240 may be formed at the distal end of a catheter shaft to provide a redirectable intravascular guidewire catheter. The catheter shaft (not shown) may have a distal end, a proximal end, a longitudinal axis, and at least one lumen extending along at least a portion of catheter shaft and the longitudinal axis of the catheter shaft. The flapper assembly 240 may have a distal end port 244, a lateral port 246, and a flapper valve or mechanism 248 with a deflectable extension 250. The deflectable extension 250 may include a biased inclined surface which may have multiple curved sections. Additionally, as shown in FIGS. 15A–B, the deflectable extension 250 may have a first position or configuration that directs a guidewire tip 254 through the distal end port 244 when the guidewire tip is positioned relatively distal to the deflectable extension 250. The deflectable extension 250 may also have a second position that directs the guidewire tip 254 through the lateral port 246 when the tip is positioned relatively proximal to the deflectable extension 250, and advanced thereafter in a relatively distal direction as shown in FIGS. 15C–D. The flapper valve 248 may be also formed with a relatively distal collar 256 that is positioned substantially adjacent to the distal end port 244. The distal collar 256 may be formed with a longitudinal length defined by the distance between the lateral port 246 and the distal port 244. At least a portion of the flapper assembly 240, including the collar portion 256, may be formed of a fluoroscopic or radiopaque material to provide an orientation marker for directional placement of the guidewire 242.

Figure 16A:
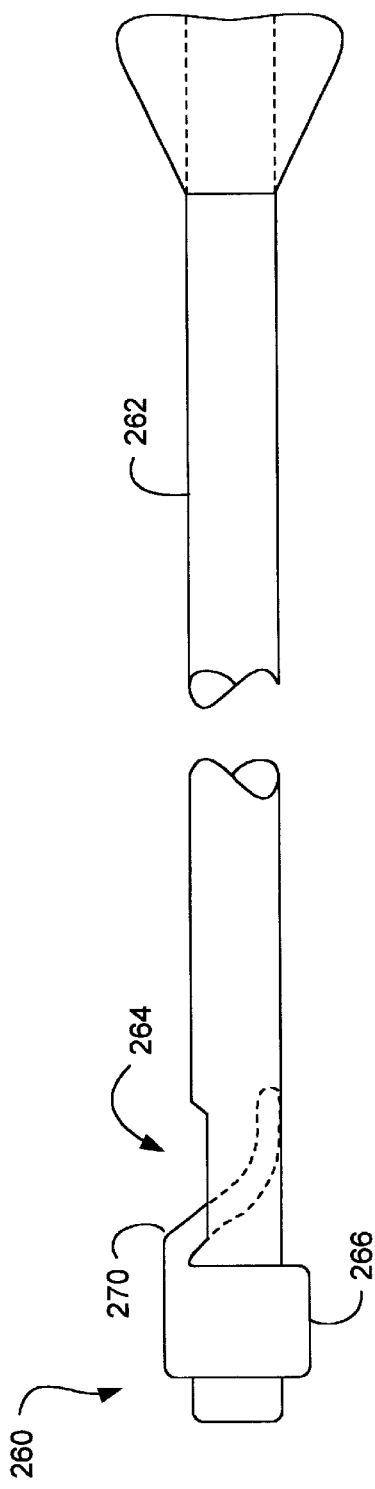
FIGS. 16A–B are simplified side views of external guidewire deflecting mechanisms that are positioned relatively outer to the catheter shaft body.
Figure 16B:
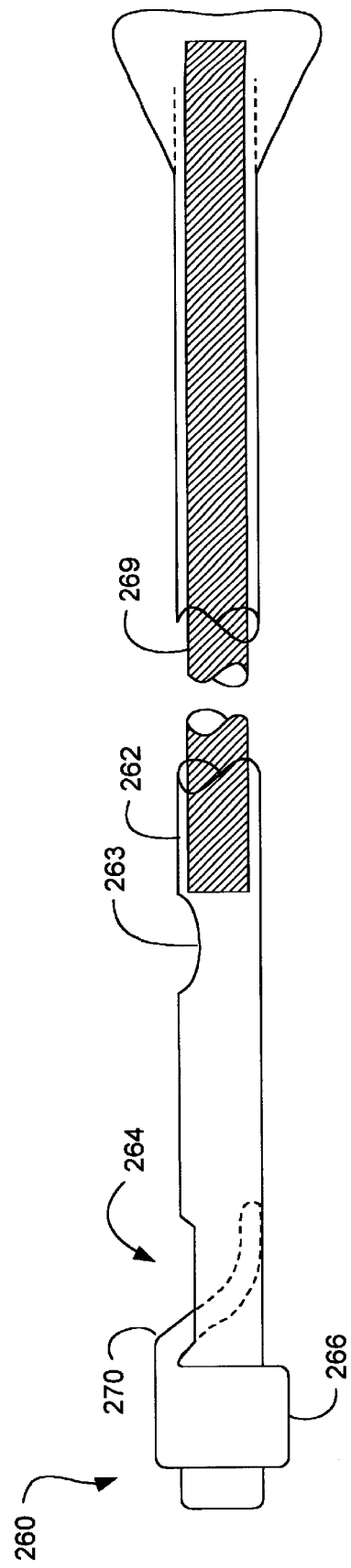

In another variation of the invention, as shown in FIG. 16A, the flapper mechanism 260 may be formed relatively externally or relatively outer to the catheter body 262. The collar portion 266 of the flapper mechanism 260 may be positioned on the outer surface of the catheter body 262 along a relatively distal portion or along any other section of the same. Furthermore, the deflectable extension 270 may be integrally formed or connected to the collar 266, and may extend through a relatively distal portion of the lateral opening 264 into the interior lumen of the catheter body 262. Although the guidewire deflectors shown in the preceding illustrations have been depicted as separate components, they may be of course integrally formed from a single piece of suitable material. In addition, as shown in FIG. 16B, a guidewire may be inserted into the interior lumen of the catheter body 262 through an opening 263 that may be formed relatively proximal to the flapper mechanism 260. The guidewire may be still positioned in at least a relatively distal portion of the interior catheter lumen. A relatively rigid or stiff member 269, which may be formed of stainless steel, may thus occupy a substantial proximal length of the catheter body lumen, to provide improved torque transmission.

Figure 17A:
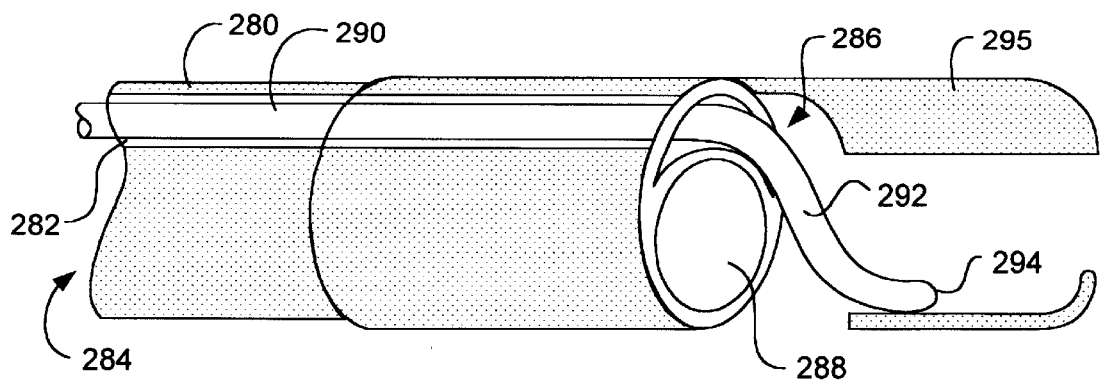
FIGS. 17A–E illustrate a redirectable guidewire catheter having a preformed actuator wire that deflects a slidable guidewire positioned within an adjacent lumen.
Figure 17B:
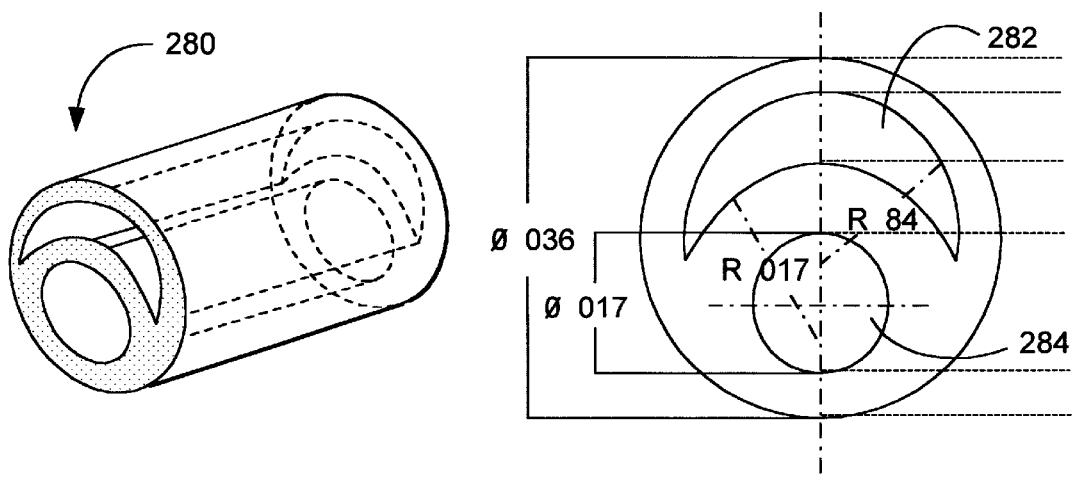
Figures 17C, 17D:
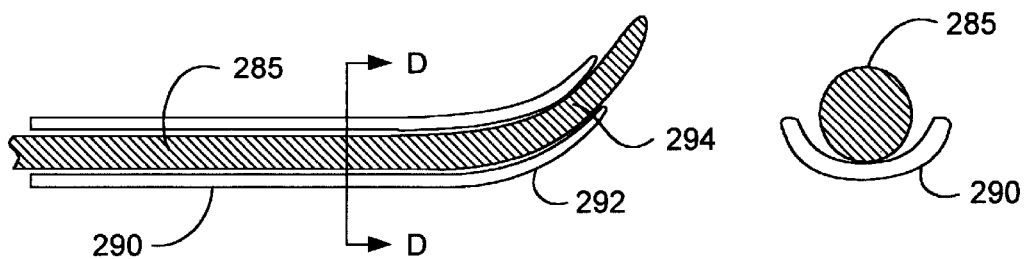
Figure 17E:
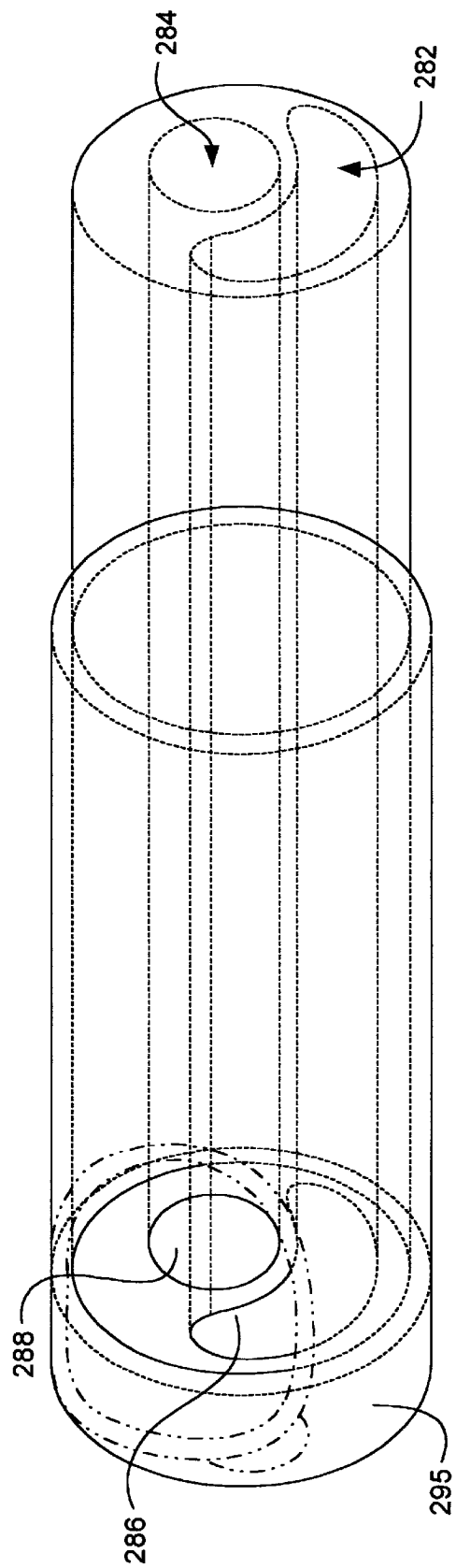

FIGS. 17A–D illustrates the distal section of a redirectable guidewire catheter. The redirectable guidewire catheter may comprise a catheter shaft 280 formed with a first lumen 282 and a second lumen 284 each extending along the catheter shaft respectively to a first distal opening 286 and a second distal opening 288. The catheter may include an actuator wire 290 slidably positioned with the first lumen 282 of the catheter shaft 280. The actuator wire 290 may be formed with a preformed distal end 292 to provide an actuated position that substantially extends or is biased towards the second distal opening 288 when advanced relatively distal through the first distal opening 286. The second distal opening 288 may be thus obstructed or at least covered in part which will tend to direct a guidewire 285 passing through the second lumen 284 and distal opening 288 away from the longitudinal axis of the catheter shaft 280. The guidewire 285 may be slidably positioned within the second lumen 284 of the catheter shaft 280, and may be deflected when advanced relatively distal through the second distal opening 288 and when the actuator wire 290 is placed in its actuated position. As shown in FIG. 17A, the actuator wire 290 may extend through the first distal opening 286 of the first lumen 282 and may still remain within an interior distal nosecone portion 295 of the catheter. The distal most tip 294 of the actuator wire 290 may be formed with a flattened portion that rests on a relatively level surface within the nosecone portion. Alternatively, the actuator wire 290 may be configured to extend outside of or beyond the outer surface of the catheter body or nosecone portion 295 (not shown). The first distal opening 286 and/or the second opening 288 may be formed at the distal most end portions of the catheter shaft 280 or at some point relatively proximal thereof. The first and second lumens 282 and 284, which lead to their respective distal openings 286 and 288, may be formed with a variety of cross-sectional configurations and positions relative to one another. For example, as shown in FIG. 17B, the actuator wire lumen 282 may be formed with a crescent or arc-shaped configuration to guide an actuator wire 290 therethrough. The guidewire lumen 284 may be formed with conventional circular cross-section and positioned side-by-side relative to the actuator wire lumen 282. The actuator wire lumen 282 may have an inner radius of about 0.017 in., and an outer radius of about 0.014 in. The guidewire lumen 284 may be also formed with a diameter of about 0.018 in. The outer diameter of the catheter shaft 280 may be about 0.036 in. These dimensions may be of course varied according to particular applications. At least a distal portion of the actuator wire 290 may be thus formed of a half-cylinder hypotube, as shown in FIG. 17C, for slidable movement within the actuator wire lumen 282. This configuration may further guide or direct a guidewire 285 extending from the adjacent lumen 284. The actuator wire 290 may of course have a proximal section formed with any other type of cross-section, and may include only a distal section that is formed with an arc-shaped region to controllably deflect the guidewire 285 in a predetermined direction.

Figure 18A:
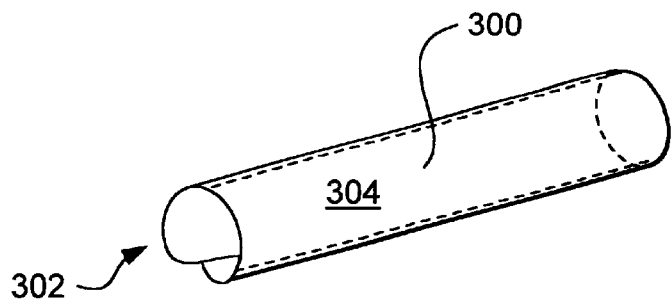
FIGS. 18A–C show the distal section of a nosecone formed with a single orifice that may be positioned at the distal end of a redirectable guidewire catheter.
Figure 18B:
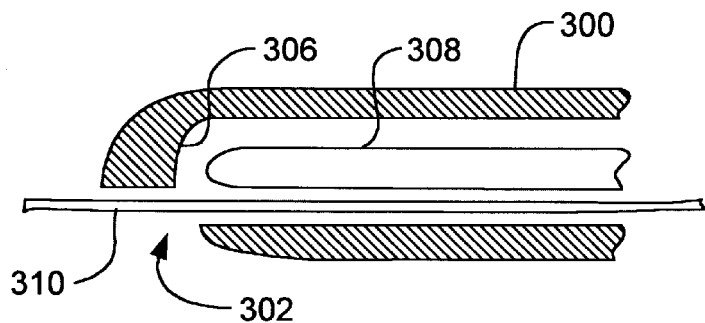
Figure 18C:
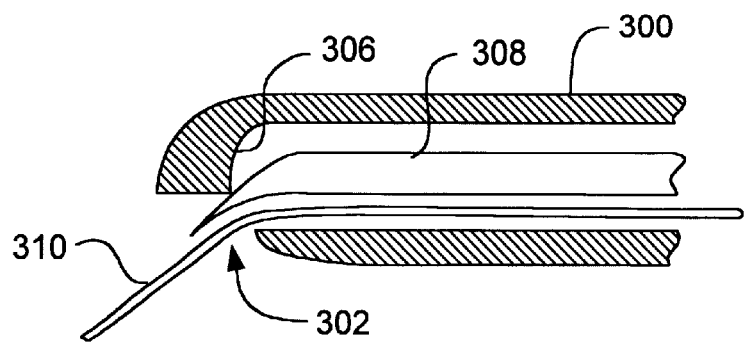

FIGS. 18A–C illustrates the distal section of a nosecone assembly 300 formed at the distal end of a redirectable guidewire catheter. The catheter may be configured for crossing a substantially occluded blood vessel, and may include a catheter shaft formed with a distal portion and a longitudinal axis, and wherein the catheter shaft has a first lumen and a second lumen each extending along the catheter shaft (see generally FIG. 17B). The first and the second lumen may be also configured in a relatively side-by-side configuration along the catheter shaft. As shown in FIG. 18A, a nosecone 300 may be formed at the distal portion of the catheter shaft (not shown), and may include a single distal orifice 302 and an interior region 304. The interior region 304 of the nosecone 302 may be formed with a tapered surface 306 that is shaped to contact an actuator wire 308. The actuator wire 308 may be slidably positioned with the first lumen of the catheter shaft. The distal tip of the actuator wire 308 may be redirected substantially away from the longitudinal axis of the catheter shaft when advanced relatively distal along the tapered surface 306 of the nosecone 300 and through the nosecone orifice 302. The actuator wire 308 may remain within the interior region 304 of the nosecone section 300, or it may extend further away from or beyond the catheter shaft to penetrate tissue in adjoining area. A guidewire 310 may be also slidably positioned within the second lumen of the catheter shaft. The guidewire 310 may be initially positioned within the selected dissection plane within a blood vessel wall, and may support positioning of the catheter in an over the wire manner. When the catheter is passed over the proximal portion of the guidewire and distally advanced, as shown in FIG. 18B, the guidewire 310 may travel in a relatively linear fashion along the longitudinal axis of the catheter shaft. However, when the distal end of the guidewire 310 is retracted into the nosecone section 302, and the actuator wire 308 extended distally, subsequent advancement of the guidewire will result in its deflection and movement away from the catheter shaft in an askew manner. As shown in FIG. 18C, the guidewire 310 is deflected away from the longitudinal axis of the catheter shaft by contacting the redirected actuator wire 308 when the guidewire is advanced relatively distal through the distal orifice 302. The orifice 302 may be formed at the distal most end of the catheter shaft or along any relatively proximal portion thereof. The catheter shaft and the nosecone 302 may be integrally formed or separately formed and joined together by conventional techniques.

Figure 19:
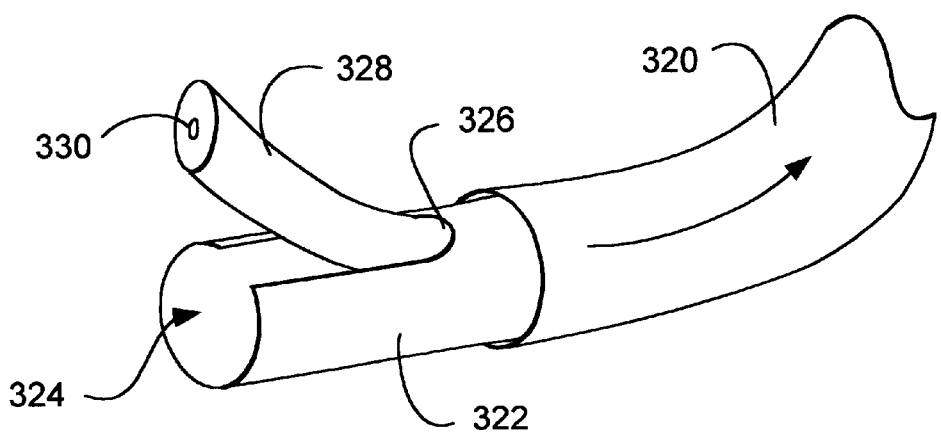
FIG. 19 is a simplified perspective illustration of the distal portion of an intravascular catheter that includes a support tube formed with a distal end portion for directing a preformed cannula.

FIG. 19 illustrates another embodiment of the invention that provides an intravascular catheter for selectively deflecting a guidewire. The catheter body 320 may be formed with a longitudinal lumen that includes a support tube 322 slidably and rotatably positioned within the longitudinal lumen of the catheter body. The support tube 322 may have a distal tube end and a tube port 324, and may also define a conduit that is in fluid communication with the tube port. The distal tube end may be also formed with a cut-out portion 326. The catheter may also include a cannula 328 having a distal cannula end, a cannula port 330 formed at its distal end, and at least one passageway extending through at least a distal end portion thereof in fluid communication with the cannula port. The distal portion of the cannula may have a preformed shape resilient curve, and may be slidably positioned within the conduit of the support tube 322. The support tube 322 may have a longitudinal axis so that the distal portion of the cannula is relatively aligned with respect to the longitudinal axis of the support tube when the cannula 328 is positioned within the support tube, and is relatively askew with respect to the longitudinal axis of the support tube when the distal cannula end extends beyond the distal end of the catheter body 320. A guidewire (not shown) may be positioned within at least a portion of the cannula passageway. When the support tube 322 and the cannula 328 are placed in a retracted position within the catheter body 320, the distal opening of the cannula 328 within the catheter may pass over the guidewire. The catheter body 320 may be moved relatively proximally so the support tube 322 extends beyond the catheter body to expose the cut-out portion 326 of the support tube. The cannula 328 within the support tube 322 may be thereafter advanced distally in order for the preformed distal cannula portion to deflect away from the longitudinal axis of the catheter body 320. The distal tip of the guidewire may be thus deflected in substantially the same direction as the distal portion of the cannula when advanced in a relatively distal direction within the cannula 328. The proximal tube end of the support tube may be also connected to a rotating assembly (not shown) to rotate the support tube relative to the catheter body. The cut-out portion 326 of the support tube 322 may be aligned in a specific manner which guides the general direction in which the distal cannula portion is pointed and extended outside of the catheter.

Figure 20:
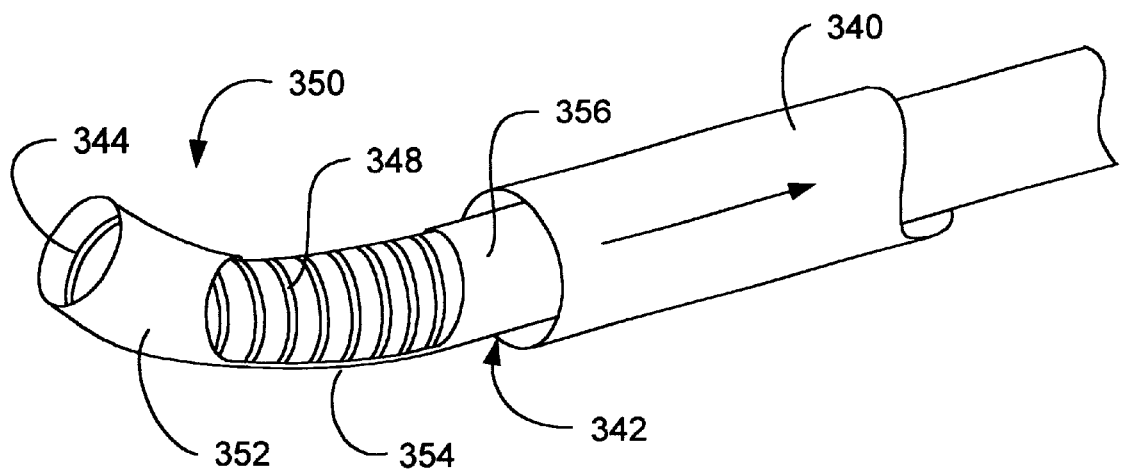
FIG. 20 is a simplified perspective illustration of the distal portion of an intravascular catheter that includes a support tube having a backbone for supporting the deflective movement of an internally positioned cannula.

Another intravascular catheter provided in accordance with the invention is further shown in FIG. 20. The catheter may also include a catheter body 340 formed with a distal end, a catheter port 342, a longitudinal axis, and a longitudinal lumen formed along at least a distal portion of the catheter body in fluid communication with the catheter port. A cannula 348 with a distal cannula end 344 may be slidably positioned within the longitudinal lumen of the catheter body 340. At least one passageway may be formed in the cannula 348 which may provide for slidable movement of a guidewire. The passageway may be in fluid communication with a cannula port formed at the distal end 344 of the cannula. The distal end 344 of the cannula may further include a support tube section 350. The support tube 350 may be formed with a distal tube end section 352, a proximal tube end section 354, and a backbone 356 connecting the distal and the proximal tube end sections. The backbone 356 of the support tube 350 may include a plurality of cut-out rib sections. The removed portions of the support tube 350 may provide reduced compression and increased flexibility of the support tube, and may support more responsive deflecting movement of the distal cannula end 344. The support tube 350 may be also preformed with a predetermined shape to deflect the distal cannula end 344 away from the longitudinal axis of the catheter body 340 when the distal cannula end is extended proximally past the distal end of the catheter body. Alternatively or additionally, the distal cannula end 344 may be preformed with a predetermined shape that deflects away from the longitudinal axis of the catheter body 340 end when extended past the distal end of the catheter body. The cannula 348 may be slidably movable within the longitudinal lumen of the catheter body 340. As with other cannulas described herein, the proximal end of the cannula may be connected to a hub assembly that provides or supports rotational or longitudinal movement of the cannula in either a relatively distal or proximal movement relative to the catheter body.

While all aspects of the present invention have been described with reference to the aforementioned applications, this description of various embodiments and methods shall not be construed in a limiting sense. The aforementioned is presented for purposes of illustration and complete description that are consistent with all applicable standards. It shall be understood that all aspects of the invention are not limited to the specific depictions, configurations or relative proportions set forth herein which depend upon a variety of conditions and variables. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications, variations or equivalents as to the described embodiments as falling within the true spirit and scope of the invention.

What is claimed is:

1. A method for crossing a substantially occluded blood vessel, said method comprising:
    selecting a guidewire with a deflectable distal tip configured for advancement within a lumen of a blood vessel wall;
    creating a longitudinal dissection plane within a wall the blood vessel by inserting the guidewire into blood vessel wall from within the blood vessel lumen at a proximal location relative to a vascular occlusion;
    forming a channel along the dissection plane within the blood vessel wall by advancing the guidewire within the blood vessel wall in a relatively distal direction; and
    selectively deflecting the distal tip of the guidewire at a relatively distal location relative to the proximal location back into the blood vessel lumen.

2. A method as recited in claim 1, wherein the blood vessel is an artery.

3. A method as recited in claim 2, wherein the artery is coronary artery.

4. A method as recited in claim 1, further comprising performing an interventional or diagnostic procedure over the guidewire.

5. A method as recited in claim 1, further comprising advancing an interventional or diagnostic catheter over the deflected guidewire from a position relatively proximal to the occlusion, through the channel, and back into the blood vessel lumen.

6. A method as recited in claim 1, further comprising imaging the occlusion and blood vessel lumen to identify their relative location to the guidewire.

7. A method as recited in claim 6, wherein the blood vessel is an artery and the imaging step comprises imaging from a position in a vein adjacent to the artery.

8. A method as recited in claim 1, wherein the distal tip of the guidewire is deflected by providing the guidewire tip with a resilient curved end, and distally advancing the guidewire from a constraining lumen into the blood vessel lumen.

* * * * *